(12) United States Patent
Ikuta et al.

(10) Patent No.: US 10,898,068 B2
(45) Date of Patent: Jan. 26, 2021

(54) MULTI-BANDWIDTH SPECTRALLY ENCODED ENDOSCOPE

(71) Applicants: Canon USA Inc., Melville, NY (US); The General Hospital Corporation, Boston, MA (US)

(72) Inventors: Mitsuhiro Ikuta, Cambridge, MA (US); Guillermo J. Tearney, Cambridge, MA (US); Dongkyun Kang, Somerville, MA (US); Dukho Do, Malden, MA (US)

(73) Assignees: Canon U.S.A., Inc., Melville, NY (US); The General Hospital Corporation, Boston, MA (US)

( * ) Notice: Subject to any disclaimer, the term of this patent is extended or adjusted under 35 U.S.C. 154(b) by 108 days.

(21) Appl. No.: 15/340,253

(22) Filed: Nov. 1, 2016

(65) Prior Publication Data
US 2018/0120555 A1 May 3, 2018

(51) Int. Cl.
*G02B 6/34* (2006.01)
*G02B 26/10* (2006.01)
(Continued)

(52) U.S. Cl.
CPC ............ *A61B 1/07* (2013.01); *A61B 1/00009* (2013.01); *A61B 1/00096* (2013.01);
(Continued)

(58) Field of Classification Search
CPC ............ A61B 1/00096; A61B 1/00172; A61B 1/0638; A61B 1/00179; A61B 1/07; G02B 23/2469
See application file for complete search history.

(56) References Cited

U.S. PATENT DOCUMENTS

| 3,976,360 A | 8/1976 | Schroder |
| 4,074,306 A | 2/1978 | Kakinuma et al. |

(Continued)

FOREIGN PATENT DOCUMENTS

| CN | 101360447 A | 2/2009 |
| CN | 101797146 A | 8/2010 |

(Continued)

OTHER PUBLICATIONS

Zeidan, A., et al., "Miniature forward-viewing spectrally encoded endoscopic probe", Optics Letters, Aug. 15, 2014, pp. 4871-4874, vol. 39, Issue 16.

(Continued)

*Primary Examiner* — Kara E. Geisel
*Assistant Examiner* — Rufus L Phillips
(74) *Attorney, Agent, or Firm* — Canon U.S.A., Inc. I.P. Divison

(57) ABSTRACT

An apparatus comprising at least: a first waveguide; a second waveguide; and a diffractive element. The first waveguide guides a first band of onto the diffractive element such that the first band is diffracted at an $m^{th}$ non-zero order over a first range of angles. The second waveguide guides a second band onto the diffractive element such that the second band is diffracted at the $m^{th}$ non-zero over the first range of angles. The second waveguide guides a third band onto the diffractive element such that the third band is diffracted at the $n^{th}$ non-zero order over the first range of angles. Wavelengths of the first band, the second band, and the third band do not overlap with each other. The $m^{th}$ order and the $n^{th}$ order are different from each other.

28 Claims, 13 Drawing Sheets

(51) Int. Cl.

| | | |
|---|---|---|
| G02B 27/42 | (2006.01) | |
| G02B 6/293 | (2006.01) | |
| G01J 3/02 | (2006.01) | |
| G02B 6/36 | (2006.01) | |
| G01J 3/18 | (2006.01) | |
| G01J 3/10 | (2006.01) | |
| G01J 3/28 | (2006.01) | |
| A61B 1/07 | (2006.01) | |
| G02B 23/24 | (2006.01) | |
| G02B 23/26 | (2006.01) | |
| A61B 5/00 | (2006.01) | |
| G02B 6/30 | (2006.01) | |
| G01J 3/36 | (2006.01) | |
| A61B 1/00 | (2006.01) | |
| A61B 1/06 | (2006.01) | |

(52) U.S. Cl.
CPC ...... *A61B 1/00172* (2013.01); *A61B 1/00179* (2013.01); *A61B 1/0638* (2013.01); *A61B 5/0075* (2013.01); *G01J 3/021* (2013.01); *G01J 3/0205* (2013.01); *G01J 3/0208* (2013.01); *G01J 3/0218* (2013.01); *G01J 3/0262* (2013.01); *G01J 3/10* (2013.01); *G01J 3/1804* (2013.01); *G01J 3/36* (2013.01); *G02B 6/2938* (2013.01); *G02B 6/29313* (2013.01); *G02B 6/30* (2013.01); *G02B 6/34* (2013.01); *G02B 6/3624* (2013.01); *G02B 23/2469* (2013.01); *G02B 23/26* (2013.01); *G02B 26/106* (2013.01); *G02B 27/4294* (2013.01); *G01J 3/2823* (2013.01)

(56) References Cited

U.S. PATENT DOCUMENTS

| | | | |
|---|---|---|---|
| 4,264,127 | A | 4/1981 | Schumacher et al. |
| 5,565,983 | A | 10/1996 | Barnard |
| 6,341,036 | B1 | 1/2002 | Tearney et al. |
| 6,478,732 | B2 | 11/2002 | Adachi |
| 6,485,413 | B1 | 11/2002 | Boppart et al. |
| 6,488,414 | B1 | 12/2002 | Dawes et al. |
| 6,522,403 | B2 | 2/2003 | Wilson et al. |
| 6,661,513 | B1 | 12/2003 | Granger |
| 6,831,781 | B2 | 12/2004 | Tearney et al. |
| 6,858,859 | B2 | 2/2005 | Kusunose |
| 7,003,196 | B2 | 2/2006 | Ghiron |
| 7,158,234 | B2 | 1/2007 | Uchiyama |
| 7,181,106 | B2 | 2/2007 | Ushiro et al. |
| 7,347,817 | B2 | 3/2008 | Glukhovsky et al. |
| 7,551,293 | B2 | 3/2009 | Yelin et al. |
| 7,796,270 | B2 | 9/2010 | Yelin et al. |
| 7,843,572 | B2 | 11/2010 | Tearney et al. |
| 7,859,679 | B2 | 12/2010 | Bouma et al. |
| 7,894,058 | B2 | 2/2011 | Wilson et al. |
| 8,045,177 | B2 | 10/2011 | Tearney et al. |
| 8,114,012 | B2 | 2/2012 | Fujita |
| 8,141,260 | B2 | 3/2012 | Pellen |
| 8,145,018 | B2 | 3/2012 | Shishkov et al. |
| 8,203,708 | B2 | 6/2012 | Lee et al. |
| 8,289,522 | B2 | 10/2012 | Tearney et al. |
| 8,780,176 | B2 | 7/2014 | Yelin et al. |
| 8,804,133 | B2 | 8/2014 | Yelin et al. |
| 8,812,087 | B2 | 8/2014 | Yelin et al. |
| 8,818,149 | B2 | 8/2014 | Shishkov et al. |
| 8,838,213 | B2 | 9/2014 | Tearney et al. |
| 9,046,419 | B2 | 6/2015 | Yelin |
| 9,090,315 | B1 | 7/2015 | Stone |
| 9,192,515 | B2 | 11/2015 | Papac et al. |
| 9,254,089 | B2* | 2/2016 | Tearney ............... A61B 1/04 |
| 9,295,391 | B1 | 3/2016 | Tearney et al. |
| 2002/0114566 | A1 | 8/2002 | Fairchild et al. |
| 2002/0145815 | A1 | 10/2002 | Moriyama et al. |
| 2003/0142934 | A1 | 7/2003 | Pan et al. |
| 2003/0223248 | A1* | 12/2003 | Cronin ............... G01J 3/10 362/555 |
| 2004/0147810 | A1 | 7/2004 | Mizuno |
| 2005/0155704 | A1 | 7/2005 | Yokajty et al. |
| 2007/0188855 | A1 | 8/2007 | Shishkov et al. |
| 2007/0233396 | A1 | 10/2007 | Tearney et al. |
| 2007/0276187 | A1 | 11/2007 | Wiklof et al. |
| 2008/0013960 | A1 | 1/2008 | Tearney et al. |
| 2008/0097225 | A1 | 4/2008 | Tearney et al. |
| 2009/0141360 | A1 | 6/2009 | Koyama |
| 2009/0153932 | A1 | 6/2009 | Davis et al. |
| 2010/0210937 | A1 | 8/2010 | Tearney et al. |
| 2011/0059023 | A1 | 3/2011 | Tunnell et al. |
| 2011/0184243 | A1 | 7/2011 | Wright et al. |
| 2011/0237892 | A1 | 9/2011 | Tearney et al. |
| 2011/0275899 | A1 | 11/2011 | Tearney et al. |
| 2012/0025099 | A1 | 2/2012 | Yelin et al. |
| 2012/0112094 | A1 | 5/2012 | Kao et al. |
| 2012/0176615 | A1 | 7/2012 | Brown et al. |
| 2013/0012771 | A1 | 1/2013 | Robertson |
| 2013/0012794 | A1 | 1/2013 | Zeng et al. |
| 2014/0071238 | A1 | 3/2014 | Mertens |
| 2014/0180131 | A1 | 6/2014 | Kamimura et al. |
| 2014/0285878 | A1 | 9/2014 | Escuti et al. |
| 2014/0309527 | A1 | 10/2014 | Namati |
| 2014/0340497 | A1 | 11/2014 | Shigeta |
| 2014/0378846 | A1 | 12/2014 | Hosoda et al. |
| 2015/0011896 | A1 | 1/2015 | Yelin et al. |
| 2015/0045622 | A1 | 2/2015 | Shishkov et al. |
| 2015/0105622 | A1 | 4/2015 | Yelin |
| 2015/0116951 | A1 | 4/2015 | Kawauchi et al. |
| 2015/0131098 | A1 | 5/2015 | Yang et al. |
| 2015/0231841 | A1 | 8/2015 | Tearney et al. |
| 2016/0320170 | A1 | 11/2016 | Yun |
| 2016/0341951 | A1 | 11/2016 | Tearney et al. |
| 2016/0349417 | A1 | 12/2016 | Tearney et al. |
| 2017/0035281 | A1 | 2/2017 | Takeuchi et al. |
| 2017/0168232 | A1* | 6/2017 | Tearney ............... G02B 23/24 |
| 2018/0017778 | A1 | 1/2018 | Ikuta et al. |
| 2018/0017806 | A1* | 1/2018 | Wang ............... G01B 9/02044 |
| 2018/0372633 | A1* | 12/2018 | Yamazoe ............... A61B 5/0066 |

FOREIGN PATENT DOCUMENTS

| | | |
|---|---|---|
| CN | 102665622 A | 9/2012 |
| JP | 2011-527930 A | 11/2011 |
| JP | 2017-505667 A | 2/2017 |
| JP | 2017-506531 A | 3/2017 |
| WO | 1999044089 A1 | 9/1999 |
| WO | 2007047690 A1 | 4/2007 |
| WO | 2013108209 A1 | 7/2013 |
| WO | 2014031748 A1 | 2/2014 |
| WO | 2014104405 A1 | 7/2014 |
| WO | 2015116951 A2 | 8/2015 |
| WO | 2015116974 A1 | 8/2015 |
| WO | 20150116939 A1 | 8/2015 |

OTHER PUBLICATIONS

Pitris, C., et al., "A GRISM-based probe for spectrally encoded confocal microscopy", Optics Express, Jan. 27, 2003, pp. 120-124, vol. 11, No. 2.

Yelin, D., et al., "Three-dimentional miniature endoscopy", Nature, Oct. 19, 2006, pp. 765, vol. 443.

Kang, D., et al., "Miniature grating for spectrally-encoded endoscopy," Lab on a Chip, 2013, pp. 1810-1816, vol. 13.

Kang, D., et al., "Spectrally-encoded color imaging", Opt Express, Aug. 17, 2009, pp. 15239-15247, vol. 17, No. 17.

Yun, et al., "High-speed spectral-domain optical coherence tomography at 1.3 μm wavelength", Opt Express, Dec. 29, 2003, pp. 3598-3604, No. 11, vol. 26.

Moharam, M.G., et al, "Formulation for stable and efficient implementation of the rigorous coupled-wave analysis of binary gratings", J. Opt. Soc. Am. A, May 1995, pp. 1068-1076, vol. 12, No. 5.

(56) References Cited

OTHER PUBLICATIONS

Tearney, G. J., Spectrally encoded miniature endoscopy, Optics Letters, vol. 27, No. 6, Mar. 15, 2002.
Wu, J. et al., Paired-angle-rotation scanning optical coherence tomography forward-imaging probe, Optics Letters, vol. 31, No. 9, May 2006.
OA issued in related U.S. Appl. No. 15/115,484 dated Aug. 3, 2017.
Wei Hui, "Introduction to Holographic Imaging", Hefei: Anhui University Press, Jan. 2013, pp. 50-52 (English translation included).

* cited by examiner

MULTI-BANDWIDTH SPECTRALLY ENCODED ENDOSCOPE

BACKGROUND

Field of Art

The present disclosure relates to spectrally encoded endoscopes.

Description of the Related Art

It is often useful and necessary for medical or research reasons to obtain images from within a subject. An endoscope or some other medical probe has the ability to provide images from inside the subject. The subject may be a human patient. Considering the risk to the subject caused by insertion of a foreign object, it is preferable that the probe be as small as possible. Additionally, the ability to image within small pathways such as vessels, ducts, needles, cuts, cracks etc., provides additional advantages to smaller probe sizes. The ideal medical probe provides as much information with the least amount of disturbance.

One method of increasing the amount of information gathered by the probe is to encode the spatial information with spectral information. In the context of endoscopy, this is referred to as spectrally encoded endoscopy (SEE) it uses wavelength to encode spatial information on a sample. Thereby, allowing high-resolution imaging to be conducted through small diameter endoscopic probes.

SEE may be accomplished by using a broad bandwidth light input into a single optical fiber. At the distal end of the fiber, a diffractive or dispersive optical element (such as a grating or prism) disperses the light across the sample, which then returns light back to a detection system. The return light may be reflected, scattered, or fluorescent light. The return light is detected by a wavelength detecting apparatus, such as a spectrometer. By detecting the light intensity as a function of wavelength, an image may be reconstructed.

The principle of the SEE technique and a SEE probe with a diameter of 0.5 mm, has been described, for example, in D. YELIN, I. RIZVI, W. M. WHITE, J. T. MOTZ, T. HASAN, B. E. BOUMA, G. J. TEARNEY, Three-Dimensional Miniature Endoscopy, Nature, Oct. 19, 2006, Volume 443, Page 765, Nature Publishing Group, London, U K, 2006 (hereinafter Yelin). Yelin's SEE probe produces images in two and three dimensions. A disadvantage of Yelin is that it does not describe how to obtain color SEE images.

US patent publication 2007/0233396 (hereinafter '396) describes a SEE technique. '396 describes an endoscope that includes a spectrally encoded confocal microscope (SECM) a spectral domain optical coherence tomograph (SD-OCT).

US patent publication 2008/0013960 (hereinafter '960) describes a second SEE technique.

By detecting the light intensity as a function of wavelength, the image may be reconstructed. However, by using wavelength information to encode spatial location, SEE images utilize much of the wavelength information to encode spatial location and therefore important color information may be lost.

Conventional endoscopy uses red green blue (RGB) color information as a cue for diagnostic purposes. For example, U.S. Pat. No. 4,074,306 describes an endoscope that obtains color images. Color has long been used as a diagnostic indicator to quickly identify abnormalities. By using wavelength information to encode spatial location, non-color SEE images utilize much of the color information to encode spatial location and therefore important color information is lost. Thus, a disadvantage of Yelin, '396, and '960 is that they do not describe how to obtain color SEE images. Since conventional endoscopy uses color information as cue for diagnosis, the formation of color images from a SEE is greatly needed.

While methods for conducting color imaging in a SEE probe have been proposed, they are lacking. In the paper, DongKyun KANG, Dvir YELIN, Brett E. BOUMA, Guillermo J. TEARNEY, Spectrally-Encoded Color Imaging, Optics Express, 17(17):15239-15247, Aug. 19, 2009, Optical Society of America, Washington D.C., 2009 (hereinafter Kang) a method of obtaining color SEE images is disclosed which uses 3 beams incident on a grating at three different angles to obtain color SEE images using a bench top setup. Kang discloses a bench top setup in which three light beams, each with one of the red, green, and blue spectral bands, were used. These light beams were incident on the grating at three different angles, which resulted in the same diffraction angle ranges for all three spectral bands. Therefore, each point on the tissue was illuminated with three spectral bands. Kang also proposes using three waveguides in a future endoscope. A disadvantage of Kang is that it requires three waveguides which increases the size of the endoscope. In addition, the system disclosed in Kang is difficult to manufacture and assemble. Multiple fibers must be sent through a multiple channel rotary junction for use in in vivo imaging. The multiple fibers increase the size of the probe, reduce the flexibility of the probe, and reduce the number of applicable uses and the invasiveness of such uses.

Another approach to making color SEE images was described in US patent publication 2011/0237892 (hereinafter '892). In '892 the spectral bands (red, green and blue) are not separated in free space or in fibers, and instead a broadband light comprising all three bands is incident on a diffractive element. The diffraction grating and angle are configured such that different orders of the different wavelength bands substantially overlap along a transverse dimension of the sample. A disadvantage of this method is that very high order diffraction (4th, 5th, 6th) is needed in order to obtain the overlapping angles.

Additionally, other solutions for color SEE which included multiple grating patterns on a small grating surface can be difficult and/or expensive to fabricate and combine into the SEE apparatus.

What is needed is an imaging system that overcomes the deficiencies of past systems, and thus provides a new color SEE probe that can provide color viewing without the size, rotary junction, or fabrication demands of prior systems.

SUMMARY

At least one embodiment is an apparatus comprising at least: a first waveguide; a second waveguide; and a diffractive element. The first waveguide may guide a first wavelength band of light onto the diffractive element such that the first wavelength band is diffracted at an $m^{th}$ non-zero order over a first range of angles. The second waveguide may guide a second wavelength band of light onto the diffractive element such that the second wavelength band of light is diffracted at the $m^{th}$ non-zero over the first range of angles. The second waveguide may guide a third wavelength band of light onto the diffractive $n^{th}$ element such that the third wavelength band of light is diffracted at the $n^{th}$ non-zero order over the first range of angles. Wavelengths of the first wavelength band, the second wavelength band, and the third wavelength band do not overlap with each other. The $m^{th}$ order and the $n^{th}$ order are different from each other.

In an embodiment, the first wavelength band may be between the second wavelength band and the third wavelength band.

In an embodiment, the first wavelength band of light may be incident on the diffractive element at a first angle. The second wavelength band of light may be incident on the diffractive element at a second angle. The third wavelength band of light may be incident on the diffractive element at the second angle.

In an embodiment, the first wavelength band of light may include green light; the second wavelength band may include blue light; and the third wavelength band may include red light.

In an embodiment, the first wavelength band of light may include green light; the second wavelength band may include red light; and the third wavelength band includes blue light.

In an embodiment, n may be equal to m minus one.

In an embodiment, n may be equal to m plus one.

An embodiment, may further comprise an optical splitter. The optical splitter may split light from a light source into the first wavelength band of light which is guided by the first waveguide; and the second wavelength band and third wavelength band of light both of which are guided by the second waveguide.

An embodiment, may further comprise the light source.

An embodiment, may further comprise a third waveguide for gathering light from a subject, wherein the subject has been illuminated with the first wavelength band, the second wavelength band of light, and the third wavelength band diffracted by the diffractive element over the first range of angles.

In an embodiment, the third waveguide may be a multi-mode fiber.

In an embodiment, the third waveguide may guide the gathered light to a spectrometer.

An embodiment, may further comprise the spectrometer.

In an embodiment, the spectrometer may include one or more detectors for converting the gathered light into an electrical signal which is then converted into a digital signal which then used to create an image of the subject.

In an embodiment, the diffracted light is scanned across the subject perpendicular to a line formed by the first range of angles.

In an embodiment, the diffracted light is scanned in a linear manner to form a planar image or in rotational manner to form a toroidal image.

An embodiment, may further comprise a moveable optical element located after the diffraction grating that scans the diffracted light.

In an embodiment, a portion of the apparatus including at least the diffraction grating is moved to scan the diffracted light.

In an embodiment, the first wavelength band may include light with a wavelength of 540 nm; the second wavelength band may include light with a wavelength of 450 nm; the third wavelength band may include light with a wavelength of 675 nm; the $m^{th}$ order is 3 or −3; the $n^{th}$ order is 2 or −2; and sgn($m^{th}$ order) is equal to sgn($n^{th}$ order).

In an embodiment, the first wavelength band includes light with a wavelength of 540 nm; the second wavelength band includes light with a wavelength of 675 nm; the third wavelength band includes light with a wavelength of 450 nm; the $m^{th}$ order is 2 or −2; the $n^{th}$ order is 3 or −3; and sgn($m^{th}$ order) is equal to sgn($n^{th}$ order).

An embodiment, may further comprise a beam blocker. The beam blocker may prevent light that leaves the diffractive element at angles that are not within the first range of angles from illuminating a sample and may allow light that leaves the diffractive element at angles that are within the first range of angles to illuminate the sample.

In an embodiment, the numerical aperture of light from the first waveguide as it is incident on the diffractive element is different from the numerical aperture of light from the second waveguide as it is incident on the diffractive element.

An embodiment, may further comprise a rotary splitter. The rotary splitter receives light from the light source, guides the first wavelength band of light from a light source to the first waveguide; guides the second wavelength band of light and the third wavelength band of light from the light source to the second waveguide; allows the first waveguide, the second waveguide and other optical components to rotate relative to the light source while allowing light to be guided from the light source to both of the first waveguide and the second waveguide.

In an embodiment, the first waveguide may guide a fourth wavelength band of light onto the diffractive element such that the fourth wavelength band of light is diffracted at the $n^{th}$ non-zero order over the first range of angles. Wavelengths of the first wavelength band, the second wavelength band, the third wavelength band, and the fourth wavelength band do not overlap with each other.

In an embodiment, the first wavelength band includes light with a wavelength of 540 nm; the second wavelength band includes light with a wavelength of 450 nm; the third wavelength band includes light with a wavelength of 675 nm; the fourth wavelength band includes light with a wavelength of 810 nm; the $m^{th}$ order is 3 or −3; the $n^{th}$ order is 2 or −2; and sgn($m^{th}$ order) is equal to sgn($n^{th}$ order)

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an endoscope as disclosed in the following which is used to inspect an inside a human body may also be used to inspect other objects.

Figure 1:
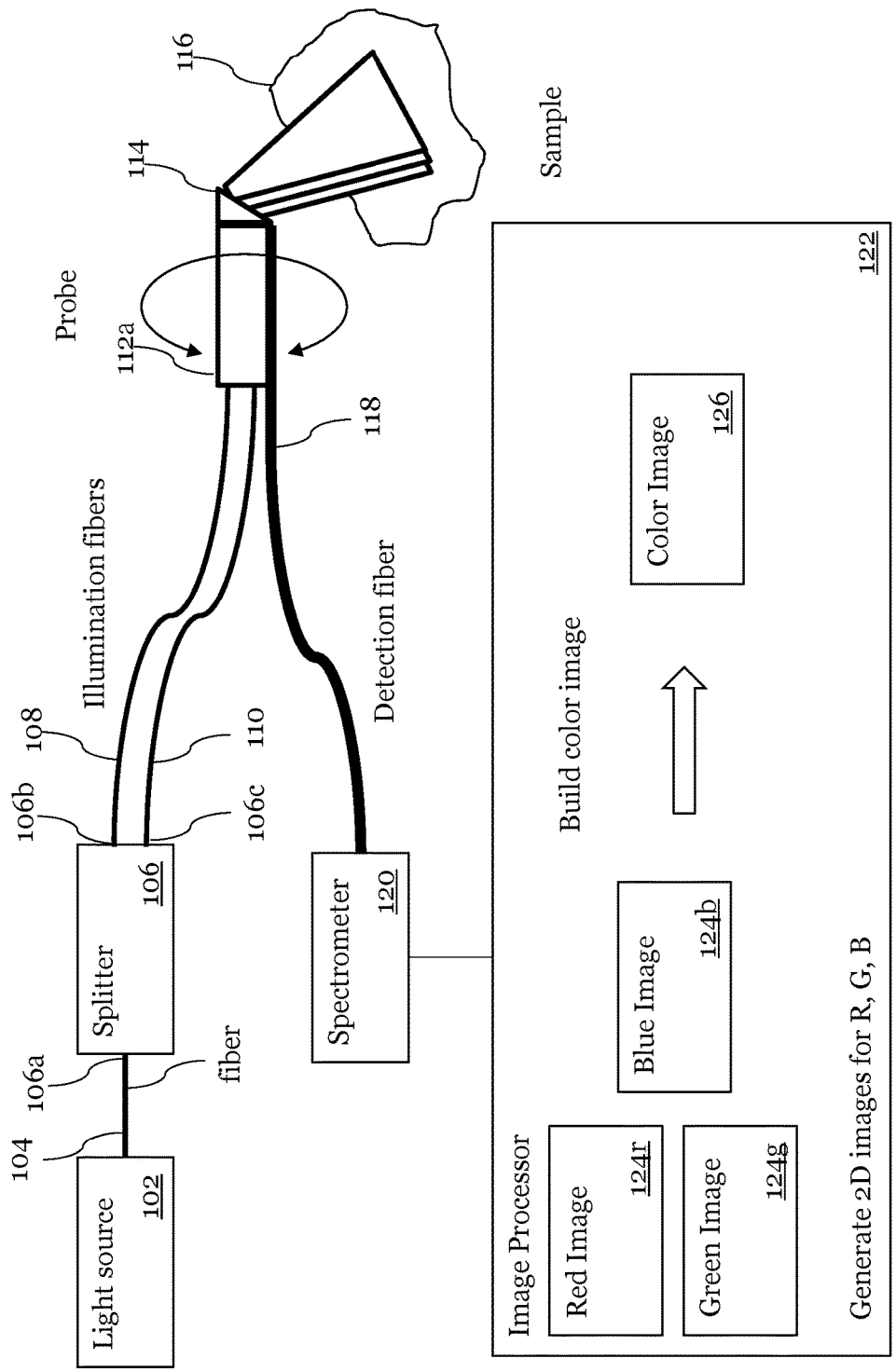
FIG. 1 is an illustration of an embodiment.

FIG. 1 is an illustration of a first embodiment, an endoscope 100 that address the issues described above with prior art systems. Endoscope 100 may include or be connected to a broadband light source 102. The broadband light source 102 may include a plurality of light sources or may be a single light source. The broadband light source 102 may include one or more of a laser, an OLED, a LED, a halogen lamp, an incandescent lamp, supercontinuum light source pumped by a laser, and/or a fluorescent lamp. The broadband light source 102 may be any light source that provides light which can then be split up into at least three bands in which each band is further dispersed to provide light which then used to for spectral encoding of spatial information. The broadband light source 102 may be fiber coupled or may be free space coupled to the other components of the endoscope 100.

Figure 2:
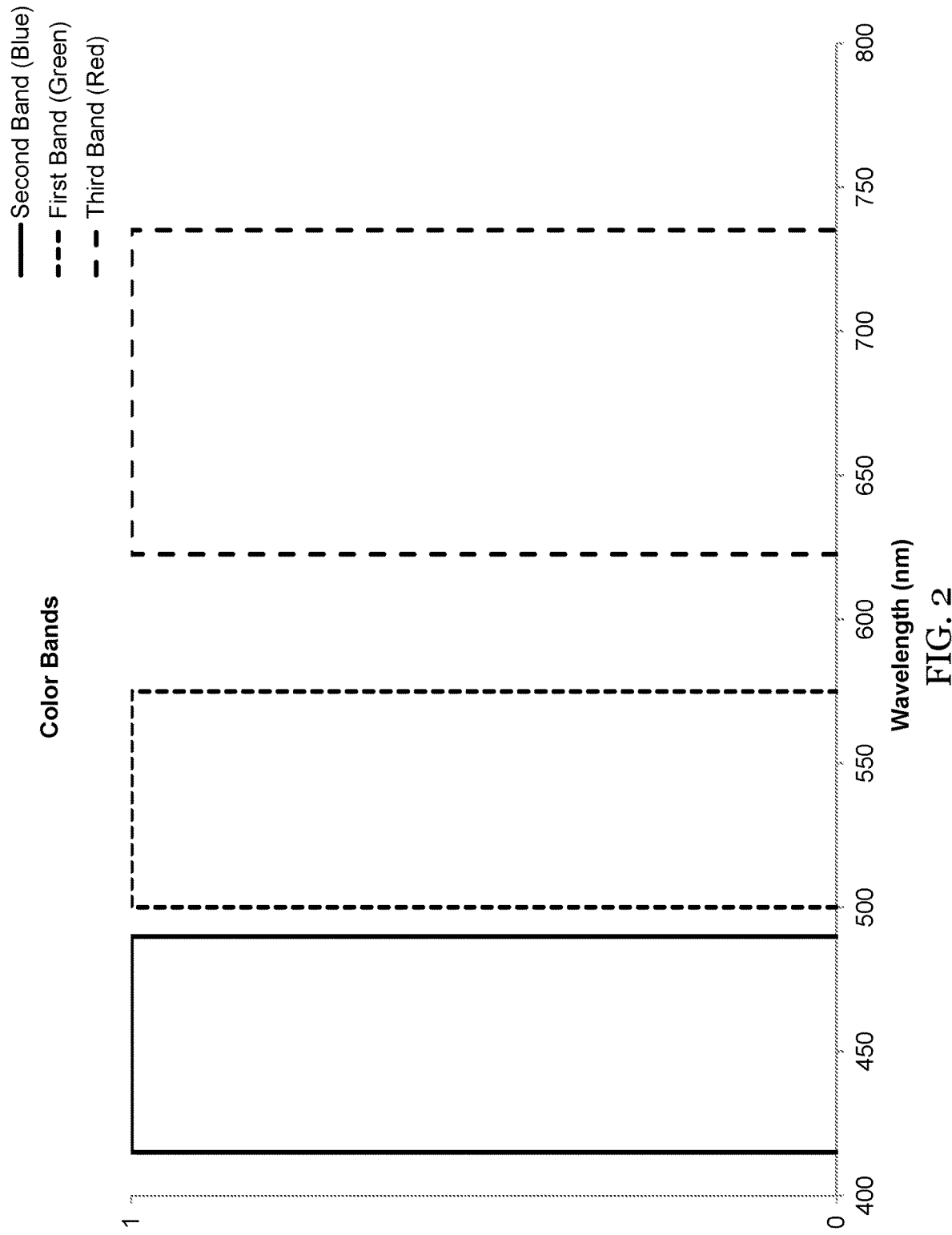
FIG. 2 is an illustration of the bands of light.

The broadband light source 102 may be connected to a fiber 104 which guides light from the broadband light source 102 to a splitter 106. The splitter 106 receives light from the broadband light source 102 via an input port 106a and outputs the light via a first output port 106b and a second output port 106c. The splitter 106 divides the received light based on the wavelength of the light. A first band of light is sent out the first output port 106b. A second band of light and a third band of light are sent out the second output port. The first band of light encompasses spectra that is between the second band of light and the third band of light as illustrated in FIG. 2. The bands of light illustrated in FIG. 2 represent the ranges of light in which the sample is illuminated with light. The spectral shape of the intensity of the light in each band is a function of the light source 102, the splitter 106, and other optics in the system 100. The spectral shape of the intensity may be compensated for during calibration. A band of light has a spectra of light between $\lambda X_1 \ldots \lambda X_N$ in which X refers to the first, second, or third bands. The wavelengths $\lambda X_1$ and $\lambda X_N$ describe the light at a threshold B % that is a percentage of the maximum intensity of the light after the splitter 106 for each band X. In one embodiment, B % may take on any non-zero number (such as 1%, 10%, 50%, 90%). The splitter 106 may be a fiber optic coupled thin film filter, a fused fiber coupler, a circulator and fiber Bragg grating combination, a planar waveguide splitter, or some other combination of optical components which splits light according to wavelength. In an alternative embodiment, the broadband light source 102 and the splitter 106 are coupled via free space. In one embodiment, the splitter includes a green dichroic mirror which reflects green light and transmits red and blue light.

The splitter 106 couples the first band of light to a first waveguide 108 via the first output port 106b. The splitter 106 couples the second band and the third band of light to a second waveguide 110 via the second output port 106c. In one embodiment, the first waveguide 108 and the second waveguide 110 are single mode fibers.

In an alternative embodiment, there is no splitter 106. Instead, the light source 102 includes at least two light sources 102a and 102b. Light from a first light source 102a couples a first band of light into the first waveguide 108. Light from a second light source 102b couples the second band and the third band into the second waveguide 110. The second light source 102a may be single broad band light source followed by a notch filter or two separate light sources one for each of the second band and the third band.

The first waveguide 108 and the second waveguide 110 are coupled to an optical system 112. The optical system 112 may include one or more optical components. The optical system may include a graded index (GRIN) lens 112a. The optical system 112 may collimate the light from both waveguides 108 and 110. The optical system 112 transmits light from the waveguides 108 and 110 to a diffraction grating 114. The optical system 112 may also include a spacer 112b between the GRIN lens 112a and the diffraction grating 114.

The diffraction grating 114 disperses light. How much the grating disperses light depends on a variety of variables. Different wavelengths of light leave the grating at different diffraction angles ($\theta_D$); The diffraction angle $\theta_D$ is a function of the wavelength of light ($\lambda$), the incident angle ($\theta_I$), the diffraction order (m), and properties of the optical components in the system 100. The incident angle of the second and third band ($\theta_{I_{BR}}$) is different from the incident angle of the first band ($\theta_{I_G}$). The diffraction grating 114 is positioned such that the light from the first band, the second band, and the third band overlap each other on the sample 116. The light may be made to overlap by carefully choosing the incident angles $\theta_I$ and the diffraction orders m associated with each band ($m_R$, $m_G$, $m_B$) in combination with each other. As illustrated in the figures below the diffraction grating 114 is a transmission grating. An alternative embodiment may also include a reflection grating without going beyond the scope of the embodiments.

In alternative embodiment, the optical system 112 may partially collimate the light from both waveguides 108 and 110 such that the light is focused onto the sample 116 but it is substantially collimated at the grating 114. In one embodiment, blue and red illumination light is guided via the second fiber 110 and green light is guided via the first fiber 108. In one embodiment, the diffraction orders ($m_R$, $m_G$, $m_B$) are (3, 3, 2).

The apparatus 100 includes a detection waveguide 118. The detection waveguide 118 may be a multimode fiber, a plurality of multimode fibers, a fiber bundle, a fiber taper, or some other waveguide. The detection waveguide 118 gathers light from the sample which has been illuminated by light that has been dispersed by the grating 114. The light gathered by the detection waveguide 118 may be reflected light, scattered light, and/or fluorescent light. In one embodiment, the detection fiber 118 may be placed before or after the grating 114. The detection waveguide 118 guides detection light from the sample 116 to a spectrometer 120.

The spectrometer 120 may include one or more optical components that disperse light and guide the detection light from the detection waveguide 118 to one or more detectors. The one or more detectors may be a linear array, a CCD, a plurality of photodiodes or some other method of converting the light into an electrical signal. The spectrometer may include one or dispersive components such as a prisms, gratings, or grisms. The spectrometer 120 may include optics and opto-electronics components which allow the spectrometer to measure the intensity and wavelength of the detection light from the sample 116. The spectrometer 120 may include an analog to digital converter (ADC).

The spectrometer 120 may transmit the digital signals to an image processor 122. The image processor 122 may be a dedicated image processor or a general purpose processor that is configured to process images. In an alternative embodiment, the image processor 122 may include an ADC and receive analog signals from the spectrometer 120. The image processor 122 may include one or more of a CPU, DSP, FPGA, ASIC or some other processing circuitry. The image processor 122 may include memory for storing image, data, and instructions. The image processor 122 generates a plurality of images including a red image 124r, a green image 124g, and a blue image 124b. The image processor 122 then combines the red image 124r, the green image 124g, and the blue image 124b into a color image 126.

One or more components of the endoscope 100 may be rotated, or oscillated so as to scan a line of illumination light two create a 2D array of illumination light. A 2D image may be formed by scanning a spectrally encoded line from the grating 114 across the sample 116. The endoscope 100 may include a junction that rotates which and couple light from the waveguides 108 and 110 to the optical system 112. An alternative embodiment, may include an optical component (mirror) after the grating 114 which rotates or scans the spectrally encoded line of illumination light across the sample 116 substantially perpendicular to the spectrally encoded line of illumination light in a linear line or circumferentially in a circle so as to produce toroidal images. Substantially in the context of the present invention means within the alignment and/or detection tolerances of the endoscope 100.

In an embodiment, the first band of light includes green light $\lambda G_1 \ldots \lambda G_N$, the second band of light includes red light $\lambda R_1 \ldots \lambda R_N$, and the third band of light includes blue light $\lambda B_1 \ldots \lambda B_N$. In one embodiment, the bands of light are: $\lambda G_1 \ldots \lambda G_N$ is 500 nm-575 nm; $\lambda R_1 \ldots \lambda R_N$ is 622.5 nm-735 nm; and $\lambda B_1 \ldots \lambda B_N$ is 415 nm-490 nm.

Figure 3:
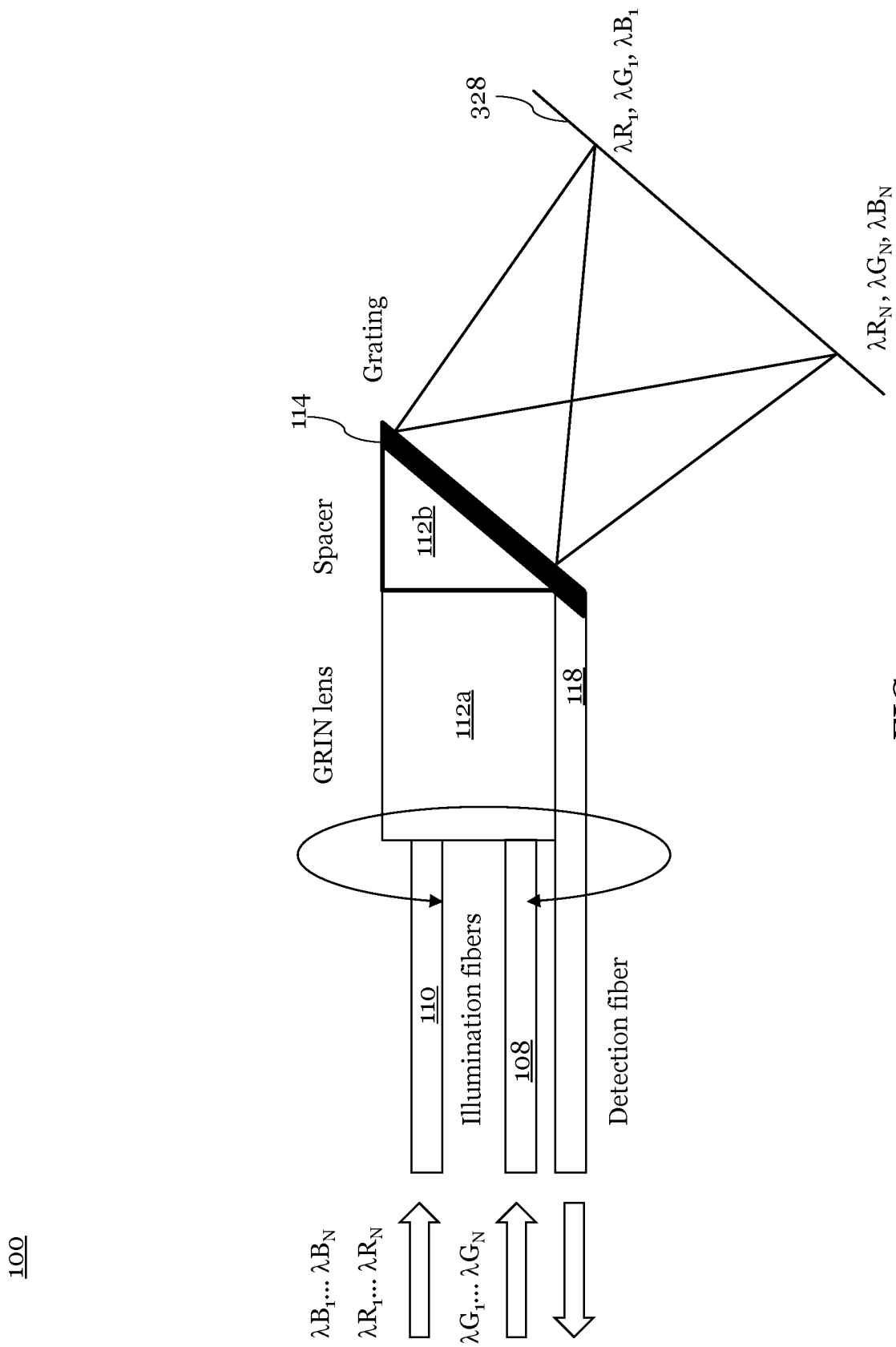
FIG. 3 is an illustration of a portion of an embodiment.

FIG. 3 is an illustration of a portion of the endoscope 100 showing the arrangement of the first waveguide 108, the second waveguide 110, the grin Lens 112a, the space 112b, the grating 114, and the detection fiber 118. As illustrated in FIG. 3 the grating disperses the light such red, green, and blue bands overlap each other forming a line 328 of illumination light, which is then scanned across an area of the sample 116. An embodiment may be a side-viewing endoscope a portion of which is rotated to obtain toroidal image of the area around the endoscope. The grating 114 may be fabricated using one or more techniques such as dry-etching, wet-etching, nano-imprint, soft lithography, direct ruling, etc. The grating 144 may be a binary grating. In an embodiment, the GRIN lens 112a is replaced with a ball lens. The illumination fibers 108 and 110 may be attached to a polished end of the GRIN lens 112a. An angle-polished spacer 112b may be position between the GRIN lens 112a and the grating 114. One or more detection fibers 118 may be are adjacent to, close by, or attached to a side surface of the GRIN lens 112a.

In one embodiment, the grating 114 is adjacent to, close by, or attached to the spacer 112b. In one embodiment, the grating is also adjacent to, close by, or attached to the detection fiber 118. In one embodiment, index matching fluid may be used between one or more of the optical components including: waveguide 108, waveguide 110, grin lens 112a, space 112a, grating 114, and waveguide 118.

Figure 4:
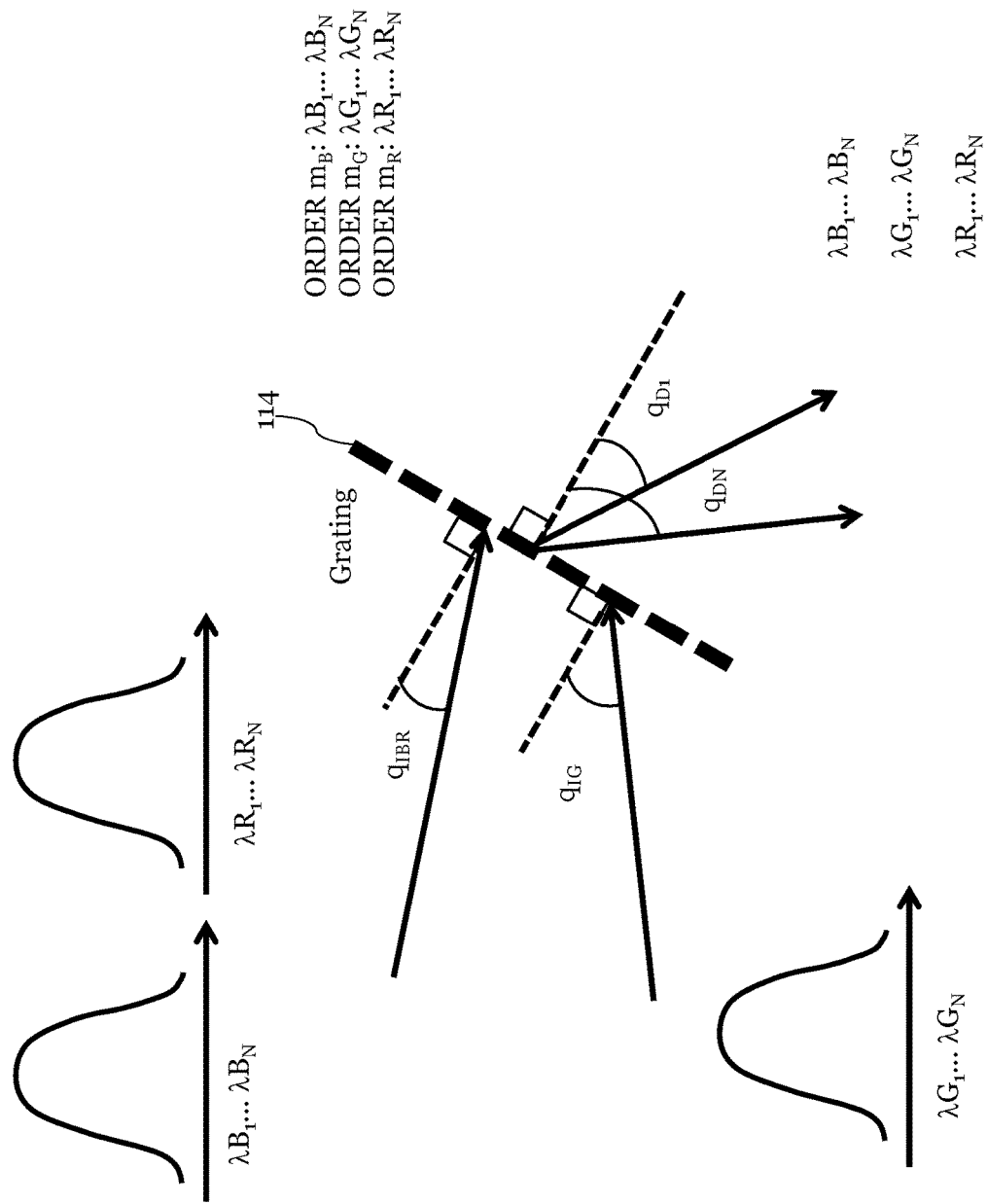
FIG. 4 is an illustration of light being diffracted in a portion of an embodiment.
Figure 5:
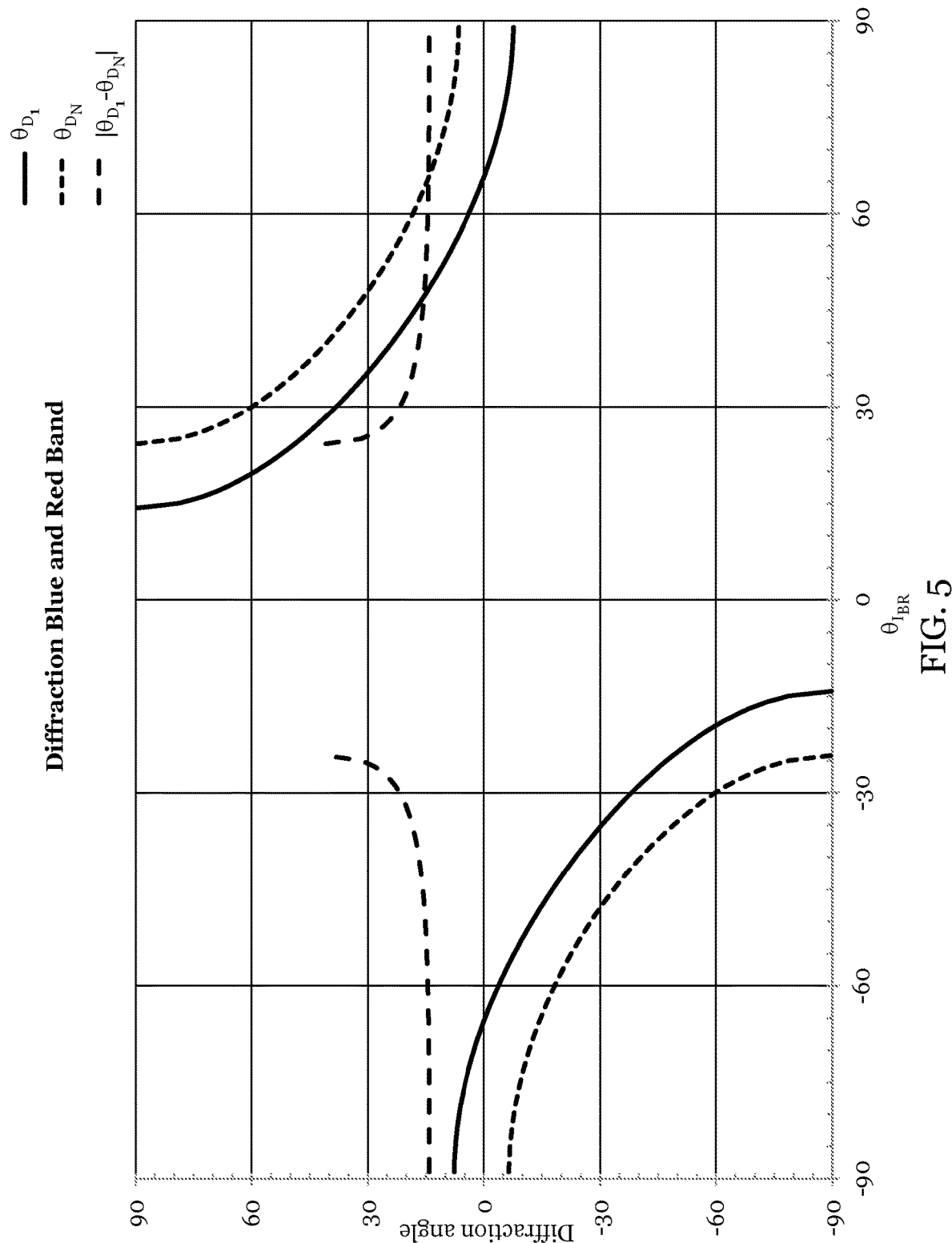
FIG. 5 is an illustration of a relationship between diffraction angle vs. incident angle in an embodiment.

FIG. 4 is an illustration of how the two incident beams travel through the spacer 112a at two different angles $\theta_{I_{BR}}$ and $\theta_{I_G}$ relative to a normal of the diffraction grating 114. In an embodiment blue, green, and red light is diffracted in the direction of the sample 116 by the grating 114. The grating 114 is designed so that at least portion of the blue, green, and red light illumination lines overlap on the sample 116. The blue light and the red light from the illumination fiber are both incident on the grating at substantially the same angle $\theta_{I_{BR}}$. As the light travels through the GRIN lens 112a and the spacer 112b the blue and red light can be slightly dispersed, the dispersion is minimal and is easily compensated for by the image processor 122. The incident angle of the green light from the first illumination fiber 108 is incident at a different angle $\theta_{I_G}$ as shown in FIG. 4. In addition, the diffraction order of the blue light $m_B$ is different than the diffraction order of the red light $m_R$. Equation (1) below is a general equation to describe the diffraction of the grating 114.

$$n_I \sin \theta_I + n_D \sin \theta_D = mG\lambda \quad (1)$$

In the context of one embodiment, the following parameters of equation (1) are: the refractive index of the spacer 112b is $n_I$; the refractive index of the medium immediately following the grating 114 before the illumination light is incident on the sample is $n_D$; the incident angle of the illumination light as it is incident on the grating 114 while in the spacer 112b is $\theta_I$; the diffraction angle of the illumination light as it leaves the grating 114 to illuminate the sample is $\theta_D$; the diffraction order is m; the groove density of the grating 114 is G; and the wavelength of the illumination light is $\lambda$.

Equation (1) may be adapted to describe the boundary conditions of the illumination light in the three bands as described by the following simultaneous equations (2) below.

$$n_I \sin \theta_{I_{BR}} + n_D \sin \theta_{D_1} = m_R G \lambda R_1$$

$$n_I \sin \theta_{I_{BR}} + n_D \sin \theta_D = m_R G \lambda R_N$$

$$n_I \sin \theta_{I_{BR}} + n_D \sin \theta_{D_1} = m_B G \lambda B_1$$

$$n_I \sin \theta_{I_{BR}} + n_D \sin \theta_{D_N} = m_B G \lambda B_N$$

$$n_I \sin \theta_{I_G} + n_D \sin \theta_{D_1} = m_G G \lambda G_1$$

$$n_I \sin \theta_{I_G} + n_D \sin \theta_{D_N} = m_G G \lambda G_N \quad (2)$$

By resolving like variables equations (2) may be converted to the following equations (3).

$$n_I \sin \theta_{I_{BR}} = m_R G \lambda R_1 - n_D \sin \theta_D = m_R G \lambda R_N - n_D \sin \theta_{D_N} = m_B G \lambda B_1 - n_D \sin \theta_{D_1} = m_B G \lambda B_N - n_D \sin \theta_D$$

$$n_I \sin \theta_{I_G} = m_G G \lambda G_N - n_D \sin \theta_{D_N} = m_G G \lambda G_1 - n_D \sin \theta_{D_1} \quad (3)$$

Gathering like terms of first equation in the set of equations (3) gives us the set of equations (4). Which sets limits on the red and blue bands for given diffraction orders.

$$m_R \lambda R_1 = m_B \lambda B_1$$

$$m_R \lambda R_N = m_B \lambda B_N$$

$$\lambda R_1 > \lambda R_N > \lambda B_1 > \lambda B_N$$

$$\{m_R, m_B \in \mathbb{Z} \mid sgn(m_R) = sgn(m_B), |m_R| < |m_B|, m_R \neq m_B \neq 0\} \quad (4)$$

In an embodiment, the wavelength of the blue band is around ⅔ of the wavelength of the red band. In one embodiment, $|m_R|$ is 2 and $|m_B|$ is 3, in which they both have the same sign. In an embodiment, the wavelength range for the blue band $\lambda B_1 \ldots \lambda B_N$ is 415 nm-490 nm, in which case the wavelength range for the red band $\Delta R_1 \ldots \lambda R_N$ is 622.5 nm-735 nm according to equation (4) above. For a given grating and optical system in which groove density G of the grating 114 is 1100 lines/mm (0.0011 lines/nm), the spacer 112b has a refractive index $n_I$ of 1.5037, and the medium outside the grating is air so the refractive index of the medium $n_D$ is 1. In which case first equation in the set of equations (3) may be simplified to equation (5) below:

$$1.5037\sin\theta_{I_{BR}} = 3*0.0011*415 - \sin\theta_{D_1} \qquad (5)$$
$$= 3*0.0011*490 - \sin\theta_{D_N}$$
$$= 2*0.0011*622.5 - \sin\theta_{D_1}$$
$$= 2*0.0011*735 - \sin\theta_{D_N}$$

$$1.5037\sin\theta_{I_{BR}} = -2*0.0011*415 - \sin\theta_{D_1}$$
$$= -2*0.0011*490 - \sin\theta_{D_N}$$
$$= -3*0.0011*622.5 - \sin\theta_{D_1}$$
$$= -3*0.0011*735 - \sin\theta_{D_N}$$

which becomes $$1.5037 \sin \theta_{I_{BR}} = 1.3695 - \sin \theta_{D_1} = 1.617 - \sin \theta_{D_N}$$

$$1.5037 \sin \theta_{I_{BR}} = -1.3695 - \sin \theta_{D_1} = -1.617 - \sin \theta_{D_N}$$

Since the sine function used in equations (5) can only have values between −1 and 1 this imposes limits on $\theta_{I_{BR}}$. In equation (5) this mean that a valid range for equation (5) in this system is describes by ranges (6). FIG. 4 is an illustration of the relationship between $\theta_{I_{BR}}$, $\theta_{D_1}$, and $\theta_{I_{BR}}$.

$$\{\theta_{I_{BR}} \in \mathbb{R} \mid -90° < \theta_{I_{BR}} < -25° \text{ and } 25° < \theta_{I_{BR}} < 90°\} \qquad (6)$$

More generally equation (6) as applied to any grating may be described by ranges (7).

$$\left\{\theta_{I_{BR}} \in \mathbb{R} \;\middle|\; -90° < \theta_{I_{BR}} < \sin^{-1}\left(\frac{m_B G\lambda B_1 - 1}{n_I}\right) \text{ and } \sin^{-1}\left(\frac{1 - m_B G\lambda B_1}{n_I}\right) < \theta_{I_{BR}} < 90°\right\} \qquad (7)$$

A reformulation of the set of equations (2) can be used to determine the relationship between $\theta_{I_{BR}}$ and $\theta_{I_G}$. We may start by rearranging set of equations (2) into set of equations (2a).

$$n_D \sin\theta_{D_1} = m_R G\lambda R_1 - n_I \sin\theta_{I_{BR}} \qquad (2a)$$
$$n_D \sin\theta_{D_N} = m_R G\lambda R_N - n_I \sin\theta_{I_{BR}}$$
$$n_D \sin\theta_{D_1} = m_B G\lambda B_1 - n_I \sin\theta_{I_{BR}}$$
$$n_D \sin\theta_{D_N} = m_B G\lambda B_N - n_I \sin\theta_{I_{BR}}$$
$$\theta_{I_G} = \sin^{-1}\left(\frac{m_G G\lambda G_1 - n_D \sin\theta_{D_1}}{n_I}\right)$$
$$\theta_{I_G} = \sin^{-1}\left(\frac{m_G G\lambda G_N - n_D \sin\theta_{D_N}}{n_I}\right)$$

Equations (2a) may be substituted into each other to give us set of equations (8) which describe the relationship between incident angle for the green light relative to the incident angle for the blue and red light.

$$\theta_{I_G} = \sin^{-1}\left(\frac{G}{n_I}(m_G \lambda G_1 - m_R \lambda R_1) + \sin\theta_{I_{BR}}\right) \qquad (8)$$
$$= \sin^{-1}\left(\frac{G}{n_I}(m_G \lambda G_1 - m_B \lambda B_1) + \sin\theta_{I_{BR}}\right)$$
$$= \sin^{-1}\left(\frac{G}{n_I}(m_G \lambda G_N - m_R \lambda R_N) + \sin\theta_{I_{BR}}\right)$$
$$= \sin^{-1}\left(\frac{G}{n_I}(m_G \lambda G_N - m_B \lambda B_N) + \sin\theta_{I_{BR}}\right)$$

In an embodiment, $\lambda G_1 \ldots \lambda G_N$ is 500 nm-575 nm are chosen in combination with the diffraction order ($m_G$) of 3 so that wavelength range overlaps with the blue and red ranges in accordance with set of equations (9). Equation (8) implies that the wavelength ranges should be set so that they are proportional to each other in accordance with the diffraction orders as described by equation (9).

$$m_B(\lambda B_N - \lambda B_1) = m_G(\lambda G_N - \lambda G_1) = m_R(\lambda R_N - \lambda R_1),$$
$$\lambda B_N < \lambda G_1 < \lambda G_N < \lambda R_1 \qquad (9)$$

The same parameters that were used in equation (5) may also be applied to the set of equations (8) in which case equation (8) becomes equations (10).

$$\theta_{I_G} = \sin^{-1}\left(\frac{0.0011}{1.5037}(3*500 - 2*622.5) + \sin\theta_{I_{BR}}\right) \qquad (10)$$
$$= \sin^{-1}\left(\frac{0.0011}{1.5037}(3*500 - 3*415) + \sin\theta_{I_{BR}}\right)$$
$$= \sin^{-1}\left(\frac{0.0011}{1.5037}(3*575 - 2*735) + \sin\theta_{I_{BR}}\right)$$
$$= \sin^{-1}\left(\frac{0.0011}{1.5037}(3*575 - 3*490) + \sin\theta_{I_{BR}}\right)$$

Figure 6:
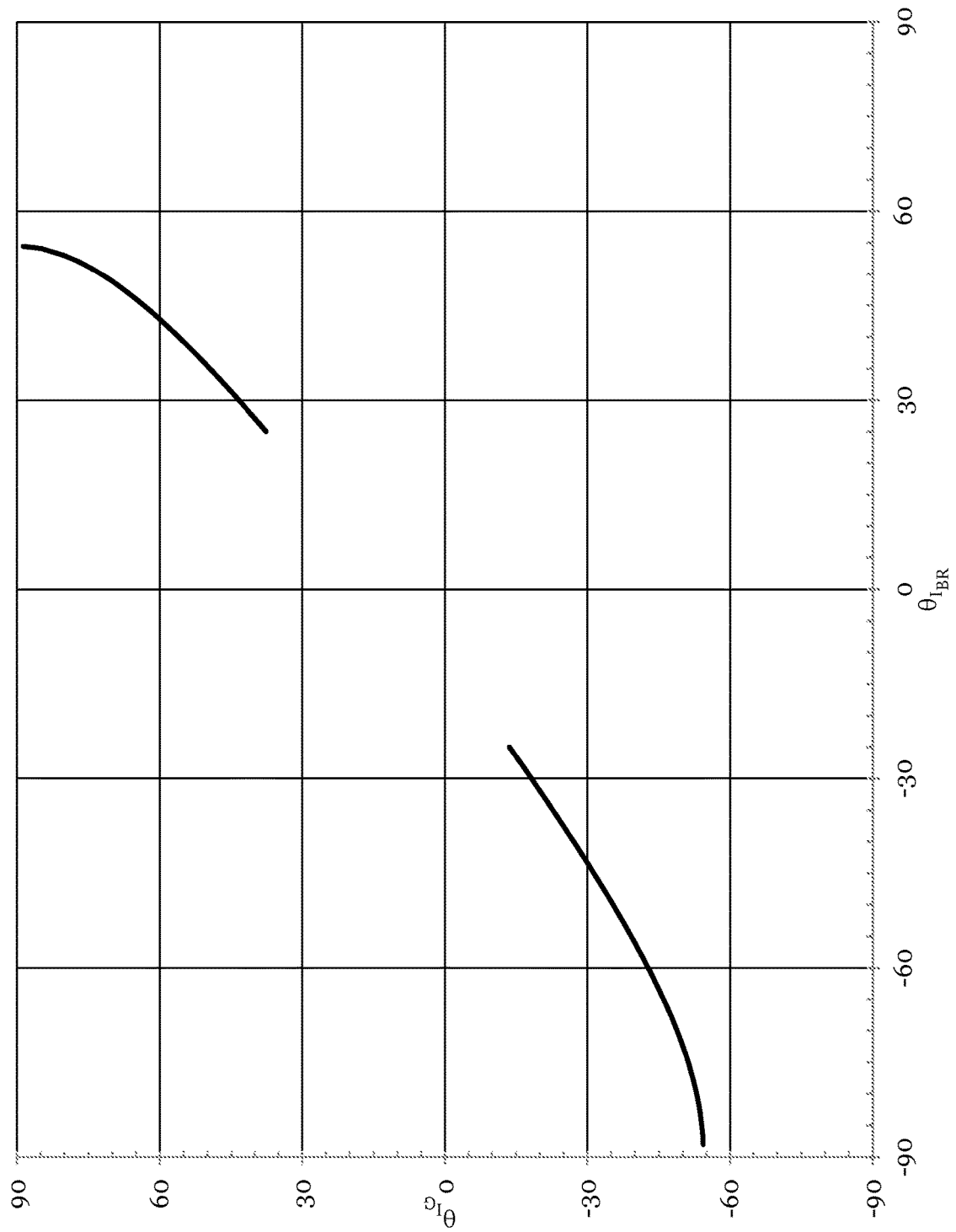
FIG. 6 is an illustration of a relationship between a first incident angle and a second incident angle.

Simplifying equation (10) gives use equation (11) as illustrated in FIG. 6. Equation (10a) describes a relationship between the two beams $\theta_{I_G}$ and $\theta_{I_{BR}}$. The set of equations (10) reduces to a single equation (11) due to the boundary condition of equation (9).

$$\theta_{I_G} = \sin^{-1}(0.1866 + \sin\theta_{I_{BR}}) \qquad (11)$$

In an embodiment, the incident angle $\theta_{I_{BR}}$ for the blue and red illumination light on the diffraction grating may be chosen to be 27.2° in which case the diffraction ranges $\theta_{D_1} \ldots \theta_{D_N}$ are approximately 43.0°-63.4°. In order for the wavelength ranges to overlap at those same diffraction ranges than incident angle $\theta_{I_G}$ for the green light should be 40.1°. In an embodiment, a spatial filter may be placed after the grating 114 such that only light exiting the grating between the diffraction ranges $\theta_{D_1} \ldots \theta_{D_N}$ is incident on the sample 116.

In an embodiment, the groove depth of the grating 114 may be 1.22 µm, and the groove opening width of the grating 114 may be 0.29 µm. By design, diffraction angle $\theta_{D_1}$ for wavelengths $\lambda B_1$, $\lambda G_1$, and $\lambda R_1$ are the same. As a consequence, the light with these 3 wavelengths is incident at one location on the sample 116. In the same way, the light of wavelengths $\lambda B_N$, $\lambda G_N$, and $\lambda R_N$ are all diffracted at the same angle $\theta_{D_N}$ and are all incident on another location on the sample 116. Thus, blue, green, and red illumination lines overlap on the sample 116.

As discussed above, the detection waveguide 118 may have the same grating 114 on it as the illumination optics. The light which is gathered by the detection waveguide 118 may first pass through the grating 114, in which cases the grating diffracts the light and may allow more light to be gathered by the detection waveguide 118. The red, green, and blue illumination light is partly reflected and/or scattered by the sample 116. The detection waveguide(s) 118 may collect part of the reflected/scattered light through the grating 114.

Back to FIG. 1, the detection waveguide 118 delivers detected light from the sample 116 to the spectrometer 120. The spectrometer 120 obtains 1D spectrum data for the 3 wavelength bands (blue, green, and red) from the detected light. In an embodiment, multiple spectrometers may be used instead of single spectrometer. The probe is rotated by a motor so that the illumination light lines scan the sample 116, and 2D data (spectrum and time) can be obtained by the spectrometer 120. An image processor 122 may generate three 2D images for red (124r), green (124g), and blue (124b) from the 2D data. In which case, one length dimension is encoded by wavelength and another length dimension is encoded by time. The image processor builds a 2D color image 126 from the 3 images 124.

The waveguides 108, 110, and 118 may be single mode fibers, multi-mode fibers, double-clad fibers, multi-core fibers, and/or planar waveguides, etc.

Using this approach with two waveguides to create three overlapping bands eases some of the problems associated with a three waveguide approach. A first obvious advantage is the number of waveguides is reduced, which makes alignment easier. This also allows for the diameter of the probe to be reduced, which improves the usefulness of the probe. This also improves the NA requirement for the lens between grating and waveguides relative to a three waveguide probe. Also lower diffraction orders may be used since wavelength ratio between Blue and Red bands is roughly 2:3, the order of diffraction to be used in this approach can be 3rd and 2nd. The aspect ratio of the grating is smaller than the grating used for 6th order diffraction which is required for the 3 fiber approach. This allows for easier fabrication of the grating.

In one embodiment, the focusing NA of the SEE probe illumination light as it is incident on the sample 116 may be less than 0.1. In a second embodiment, the focusing NA of the SEE probe illumination light as it is incident on the sample 116 is less than 0.05. In a third embodiment, the focusing NA of the SEE probe illumination light as it is incident on the sample 116 is less than 0.025.

Diffraction Orders

An embodiment may be described in terms of the incident angle difference between 2 color channels using two different fibers. An embodiment may be described in terms of an inequality about incident angles of the two different fibers of the 2 color channels and other parameters.

An embodiment may include a G-channel (green) as a middle channel between a B-channel (blue) and a R-channel (red) in terms of wavelength. The B-channel and the R-channel may use the same fiber. That is, $\theta_{I_B} = \theta_{I_R}$. The G-channel may use a different fiber from the B-channel and the R-channel.

In one embodiment, the diffraction order associated with the B-channel and the G-channel are the same; and the diffraction order associated with R channel is different. While in a different embodiment, the diffraction order associated with the R-channel and the G-channel are the same and the diffraction order associated with B channel is different.

Setting Wavelength Ranges for an Embodiment

In an embodiment, wavelength differences for light incident on the same location of the subject (tissue) between blue and green, or, green and red channels, should be larger than 50 nm. Otherwise, it may be difficult to efficiently use visible spectrum.

In one embodiment, the diffraction orders ($m_R$, $m_G$, $m_B$) are (2, 3, 3), in which case equation (8) may be adapted to describe this embodiment as described in equation (12) below. In which the variables $\lambda X_i$ represent wavelengths of light in each band associated with an overlapping position i on the sample.

$$n_I(\sin\theta_{I_G} - \sin\theta_{I_{BR}}) = m_G G(\lambda G_i - \lambda B_i) > m_G G(50 \text{ nm}) \quad (12)$$

In another embodiment, the diffraction orders ($m_R$, $m_G$, $m_B$) are (2, 2, 3), in which case equation (8) may be adapted to describe this embodiment as shown in equation (13) below:

$$n_I(\sin\theta_{I_{BR}} - \sin\theta_{I_G}) = m_G G(\lambda R_i - \lambda G_i) > m_G G(50 \text{ nm}) \quad (13)$$

Equations (12) and (13) may be combined to describe the relationship between the incident angles of the light from the two waveguides in and equation (14) below.

$$\frac{n_I |\sin\theta_{I_G} - \sin\theta_{I_{BR}}|}{m_G G} > 50 \text{ nm} \quad (14)$$

Equations (12)-(13) may be described in terms of a common parameter $\Delta\lambda$ which is defined below in equation (15). The common parameter $\Delta\lambda$ may vary depending on the resolution of the spectrometer, the dispersion of the grating, and/or variability in the reflectance of the sample.

$$\Delta\lambda = \lambda G_i - \lambda B_i \text{ or } \Delta\lambda = \lambda R_i - \lambda G_i \quad (15)$$

In an embodiment, the common parameter $\Delta\lambda$ may be 30 nm, 50 nm, or 70 nm which describes the difference in wavelength of two of the at least three wavelengths which are incident on the same spot of the sample. Equation (14) may also be more generally rewritten in terms of equation (15) as equation (16) below:

$$\frac{n_I |\sin\theta_{I_G} - \sin\theta_{I_{BR}}|}{m_G G} > \Delta\lambda \quad (16)$$

Equations (4) and (9) above describe some of the limitations on the edges of wavelength bands used in an embodiment in addition the edges of the wavelength bands should not overlap as described by the relation (17) below:

$$\lambda B_1 < \lambda B_N < \lambda G_1 < \lambda G_N < \lambda R_1 < \lambda R_N \quad (17)$$

In an embodiment, a splitter 106 may be chosen such that there is a gap between: $\lambda B_N$ and $\lambda G_1$; and between $\lambda G_N$ and $\lambda R_1$. The splitter 106 may include a dichroic mirror or other filters which have a finite slope in transmission/reflection spectrum. For example, 10 nm, 15 nm, or 20 nm may be set as the gap between 2 wavelengths to take the finite slope into account.

In a typical embodiment, wavelengths around 400 nm and under are too short for practical use due to absorption of the typical optical material (glass) at this wavelength. Special embodiments using specially designed materials may be used for wavelengths around 400 nm and below. An embodiment may set $\lambda B_1$ to be greater than 405 nm, 410 nm, or 415 nm.

A typical embodiment, may be designed to be used to view a sample that includes hemoglobin. The absorption spectrum of hemoglobin has a significant slope around 600 nm which has an impact on the reflectance of a sample. Since the spectra is used to encode location this slope around 600 nm impacts the ability of the SEE if a wavelength around 600 nm is used to encode location. Therefore, an embodiment may avoid using wavelengths around 600 nm to encode location. Alternative embodiments may be designed taking changes in the reflectance of the sample into account when choosing which wavelength ranges are used to encode location.

For a typical embodiment, $\lambda B_1$ may be set to be 415 nm and $\lambda G_1$ may be set to 500 nm. The diffraction orders ($m_R$, $m_G$, $m_B$) may be set to be (2, 3, 3). Based on equation (4), $\lambda R_1$ should be 622.5. The wavelength band edge $\lambda G_1$ may be set to 500 nm, this may allow an embodiment to avoid the 600 nm slope referenced above. In an embodiment, a gap between $\lambda B_N$ and $\lambda G_1$ may 10 nm, therefore $\lambda B_N$ may be set to be 490 nm. The wavelengths $\lambda G_N$ and $\lambda R_N$ may then be determined using equation (9) which ensures that all the wavelength bands overlap and have same FOV. Therefore, $\lambda G_N$ is set to 575 and $\lambda R_N$ is set to 735.

Once the wavelength bands are set the dichroic mirrors (or other filters) may be chosen based on these wavelength bands. Corresponding performance (for example transmittance/reflectance) should have enough quality, for example, >50%, >70%, and >90% for each color channel wavelength band.

One or more optical components (such as the GRIN lens 112a and the spacer 112b) other than the grating 114 have some chromatic dispersion. This chromatic dispersion may slightly shift positions of the edges of the wavelength band but this shift should be at most 10 nm and more likely less than 1 nm or 0.1 nm for a typical sized endoscope. The amount of chromatic shift is proportional to the length of the optical components.

The design of an embodiment involves the setting of at least 6 wavelengths. Once the diffraction orders of each band are chosen, 3 of those wavelengths are dependent upon boundary conditions defined in equations (4) and (6). In other words, there are 3 degrees of freedom in choosing the 6 wavelengths. For example, in an embodiment, the combination of diffraction orders may be determined first. Next, three of the four wavelengths ($\lambda B_1$, $\lambda B_N$, $\lambda G_1$, $\lambda G_N$) may be chosen. The other 3 wavelengths of the 6 wavelengths are determined based on the chosen wavelengths and equations (4) and (9). The wavelengths are chosen to satisfy the wavelength gap requirement between the blue channel and the green channel, and between the green channel and the red channel. While the wavelength boundaries may be chosen to avoid certain wavelengths such as below 400 nm and the Hemoglobin slope around 600 nm these are not requirements and change depending upon the application of the embodiment.

Filters (e.g. dichroic mirror) are chosen so that they satisfy performance requirement for those wavelength bands. For example, transmittance/reflectance is more than 50%.

While this embodiment has been described in terms of a three wavelength band system. The system may be extended to a 4 or 5 wavelength band system.

Second Embodiment

Figure 7:
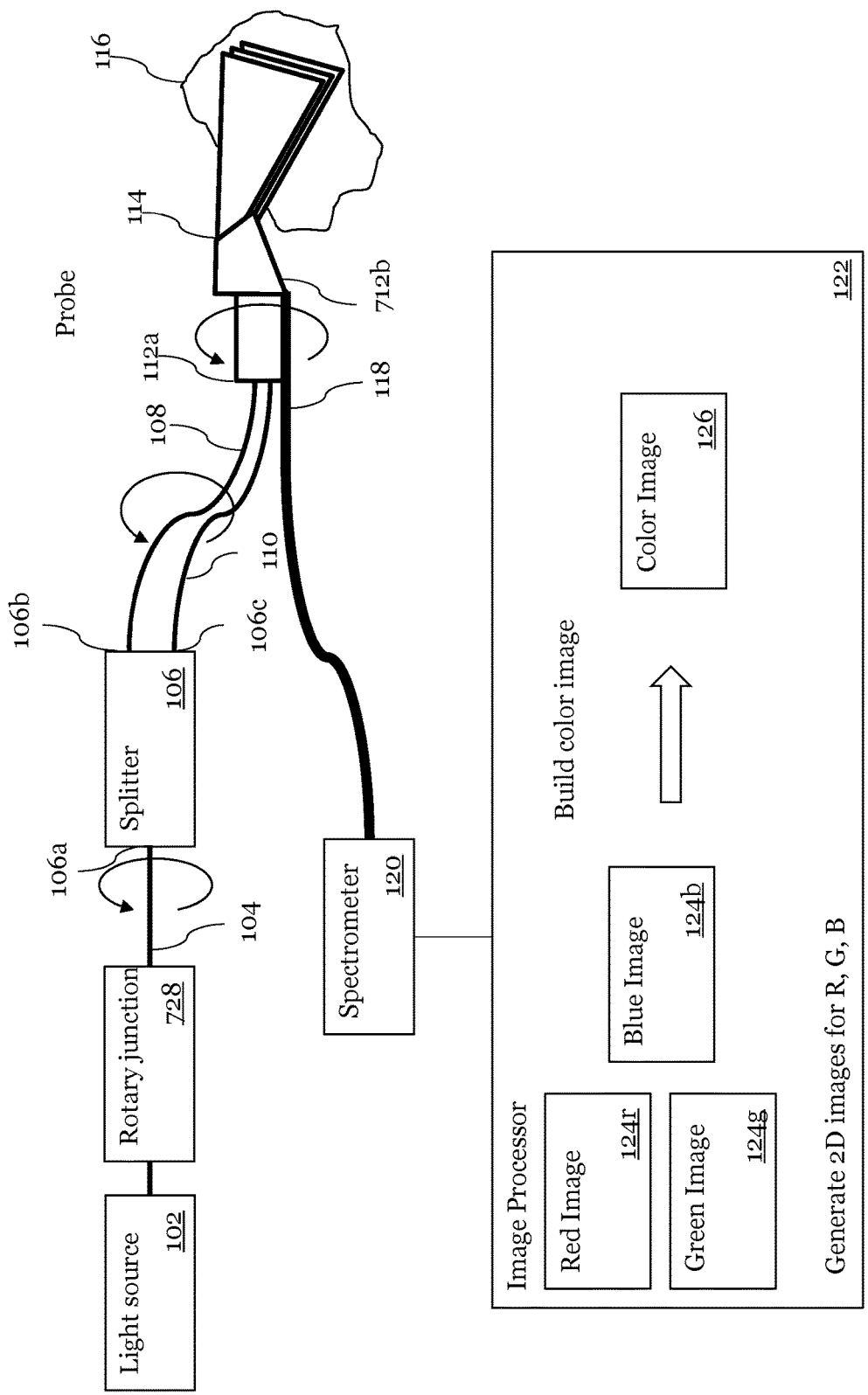
FIG. 7 is an illustration of an embodiment.

FIG. 7 is an illustration of a second embodiment 700 that includes a forward view and a rotary junction. The SEE system 700 illustrated in FIG. 7 is substantially similar to the SEE system 100 illustrated in FIG. 1. The SEE system 700 includes a probe, a light source 102, a spectrometer 120, and an image processor 122. Portions of the SEE system 700 which are substantially similar or identical to the portions of the SEE system 100 will not be discussed in detail.

The probe in the second embodiment is forward viewing probe as opposed to a side viewing probe. The probe includes a spacer 712b which couple light to the grating 114 in such a manner that the light is diffracted in the forward direction. The spacer 712b may be include a reflective surface or make use of total internal reflection to guide light to the grating 114.

The probe in the second embodiment may also be rotated continuously by a rotary junction 728 that is between the light source 102 and splitter 106. The rotary junction may be a ball lens or some other optical rotary junction. The connection between the light source 102 and the rotary junction 728 may be a free space coupling or a fiber coupling. The rotary junction may supply just illumination light via the rotary coupling or may supply one or more of illumination light, power, and/or sensory signal lines.

Figure 8:
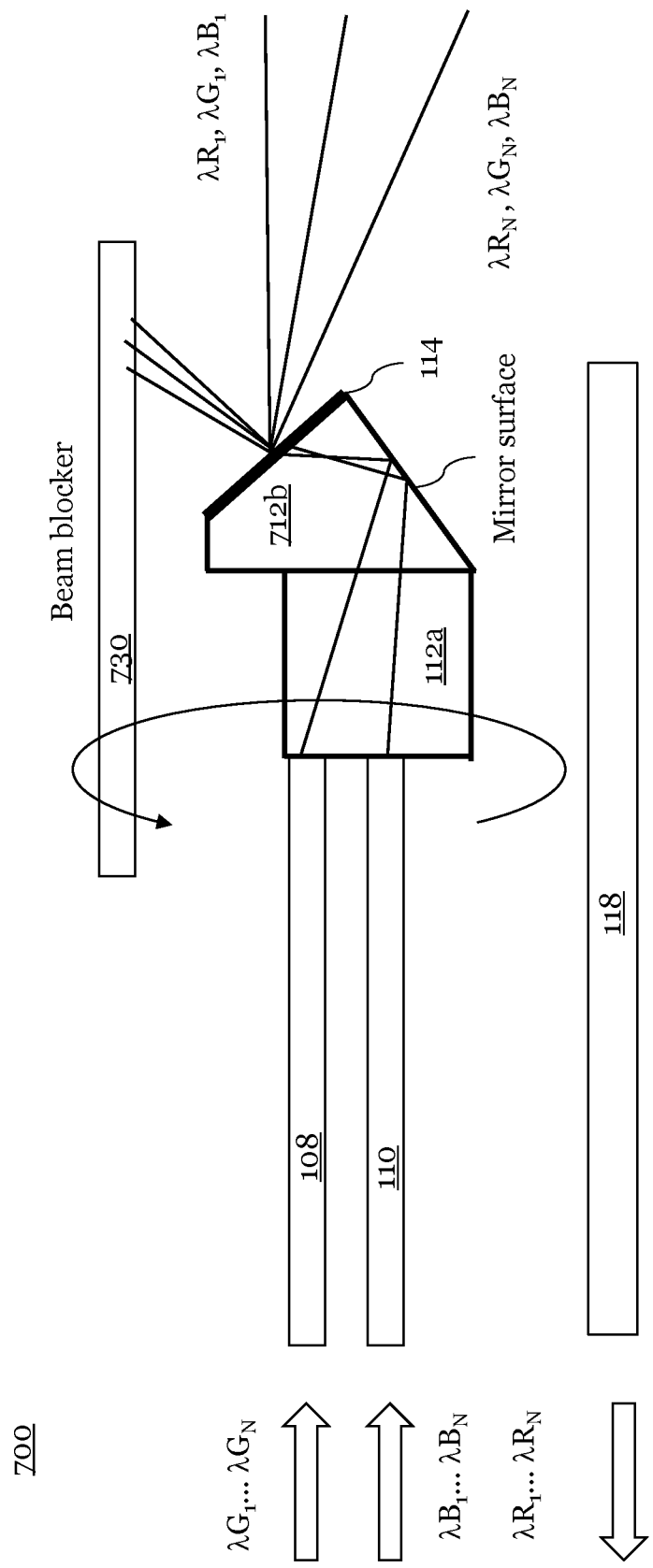
FIG. 8 is an illustration of a portion of an embodiment.

FIG. 8 is an illustration of a portion of the forward viewing SEE probe as used in the second embodiment 700. The two illumination waveguides 110 and 108 may be attached to an end surface of a GRIN lens 112a. An angle-polished spacer 712b may be attached to the other end surface of the GRIN lens 112a. Index matching fluid may be between the angle-polished spacer 712b and the GRIN lens 112a. The angle-polished spacer 712b and the GRIN lens 112a may be glued together. The angle-polished spacer 712b and the GRIN lens 112a may be pressed together at a specified pressure. One of the polished surfaces of the angle-polished spacer 712b may work as mirror to bend the light from the illumination waveguides 110 and 108. In an alternative embodiment, a reflective coating may be placed on one or more of the surfaces of the angle-polished spacer 712b.

The grating 114 may be made on another of the polished surfaces of the angle polished spacer 712b. The grating 114 and the angle-polished spacer 712b may be combined into a single grism. In one embodiment, the grating may be attached to angle-polished spacer 712b via index matching fluid, glue, and/or they may be pressed together at a specified pressure.

As in the first embodiment blue (including wavelengths $\lambda B_1 \ldots \lambda B_N$) and red light ($\lambda R_1 \ldots \lambda R_N$) are coupled into one (110) of the waveguides, and green light ($\lambda G_1 \ldots \lambda G_N$) are coupled into the other waveguide (108). Since the two illumination fibers are separated on the GRIN lens, the blue/red light and the green light from the fibers are incident on the mirror surface of the angle-polished spacer 712b at different angles, and so they are also incident on the grating 114 at different angles.

The parameters of the grating (refractive index, groove density, groove depth, groove opening width, and order of diffraction), spacer angles, location of fibers, and the numerical aperture (NA) of the GRIN lens are chosen so that the blue, green, and red light illumination lines overlap on the sample. For example, all the parameters for the first embodiment are still relevant for this second embodiment.

In addition, the diameter of the angle-polished spacer 712b may be 500 µm. The diameter of the GRIN lens 112a can be 500 µm. The angle between probe axis and mirror surface normal may be 54.5°. The NA of the GRIN lens 112a may be 0.34. In one embodiment, the fiber offset $\Delta r_G$ is +165 µm for waveguide 108 relative to the center of the GRIN lens 112a and the fiber offset $\Delta r_{BR}$ is −10 µm for waveguide 110 relative to the center of the GRIN lens 112a.

In one embodiment, the focusing NA of the SEE probe at the sample may be less than 0.1. In most cases, it is less than 0.05, and is often less than 0.025.

The probe of the second embodiment 700 may include one or more detection waveguide(s) 118. In one embodiment, the detection waveguide(s) 118 are not rotated. The detection waveguide(s) 118 collect light scattered/reflected from the sample 116, and deliver the light to the spectrometer 120.

The probe of the second embodiment 700 may have a beam blocker 730 to prevent light diffracted in lower orders from illuminating the sample 116. For example, if 3rd/3rd/2nd order diffraction is used for blue/green/red for illumination, this beam blocker 730 can be used to block light diffracted in 2nd/2nd/1st order (and lower order) for blue/green/red. The beam blocker 730 can prevent such light from illuminating the sample 116 which is then absorbed, scattered, and/or reflected by the sample 116. The beam blocker 730 rotates together with the illumination optics.

One or more optical components may be added between the grating 114 and the sample 116 to increase field of view. The optics may be static. For example, they may include a lens.

Third Embodiment

Figure 9:
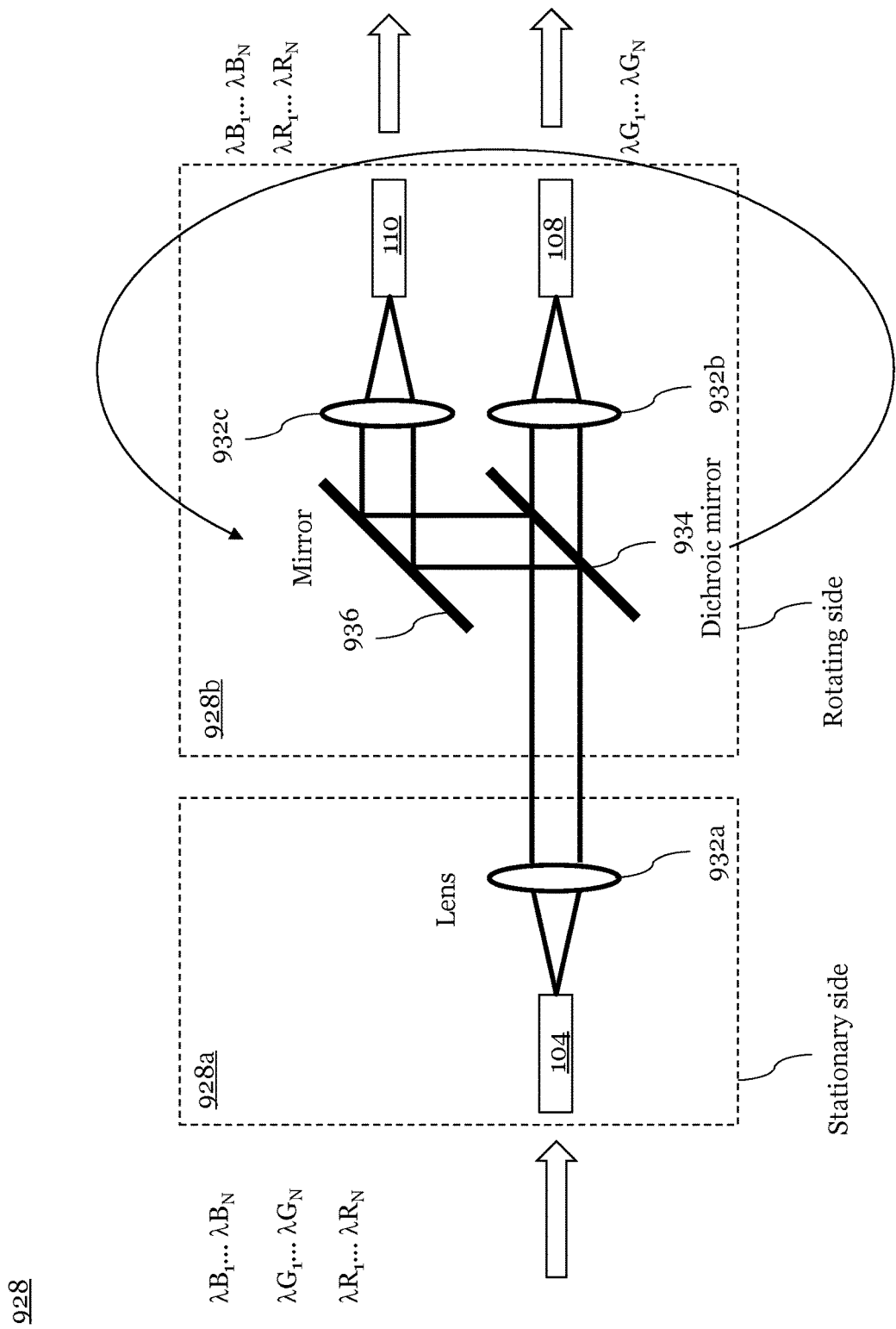
FIG. 9 is an illustration of a portion of an embodiment.

FIG. 9 is an illustration of a portion of an alternative embodiment of SEE in which the splitter 106 and the rotary junction 728 are combined into a rotary splitter 928. A waveguide 104 may be connected to the light source 102 at the stationary side 928a of the rotary junction 928a. The illumination waveguides 108 and 110 attached to the probe are on the rotating side 928b of the rotary splitter 928. Light from waveguide 104 may be collimated by a lens 932a. The collimated light is divided into 2 paths by a dichroic mirror 934. The dichroic mirror 934 is transparent to green light, and reflects blue light and red light. The green light is coupled to the waveguide 108 through a lens 932b. The blue light and red light are coupled to the waveguide 110 through a mirror 936 and a lens 932c. The dichroic mirror 934, the mirror 936, and the lenses 932b-c are rotated together along with the illumination waveguides 108 and 110. The axis of rotation may be centered on the axis of waveguide 108 where the illumination is initially coupled to the waveguide by the lens 932b.

Fourth Embodiment

Figure 10:
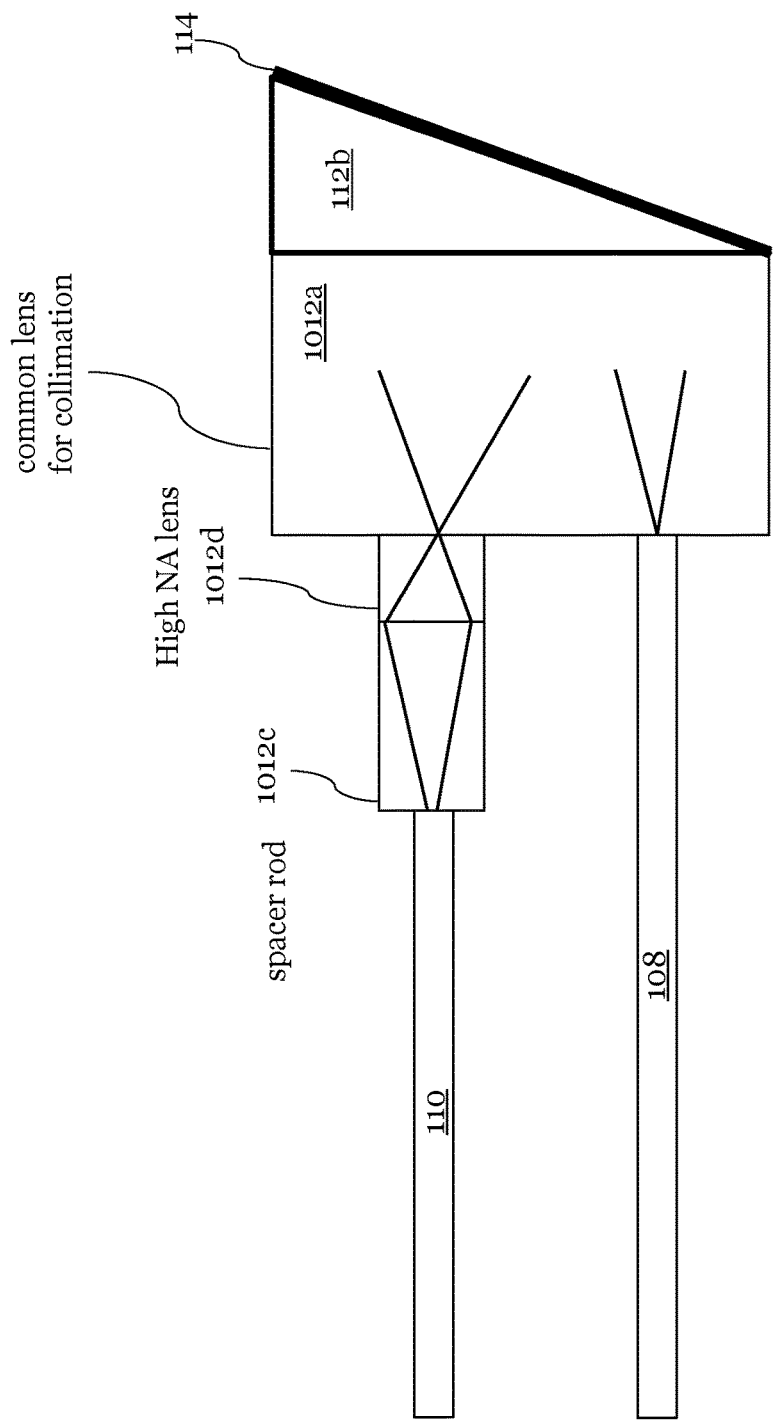
FIG. 10 is an illustration of a portion of an embodiment.

FIG. 10 is an illustration of a portion of an embodiment in which a high NA lens is used in the SEE probe, that is substantially similar to the probe 100 illustrated in FIG. 1. The high NA system may also be adapted to the SEE probe illustrated in FIG. 7. As shown in FIG. 10 another lens 1012d may be inserted between one of the illumination waveguides 110 and collimation lens 1021a attached to the spacer 112b to change the NA of the illumination light. In one embodiment, the illumination waveguide 108 couples light to a first lens 1012a. The illumination waveguide 110 may also be coupled to a spacer rod 1012c. Light from the spacer rod 1012c may also be coupled to a high NA lens 1012d. Light from the high NA lens 1012d may be coupled to the lens 1012a. The first lens 1012a may couple light to the spacer 112b which is then diffracted by grating 114. In an alternative embodiment, waveguides 108 and 110 are switched. In an alternative embodiment, an additional spacer rod and lens are added between lens 1012a and waveguide 108.

The applicants have found that it is sometimes advantageous to fill the grating 114 with illumination light. It also sometimes advantageous to adjust the spot size of illumination light as it exits each waveguide independently. This allows for greater design freedom. It is therefore, effective to put high NA lens for one or each of the two illumination waveguides.

Fifth Embodiment

Figure 11:
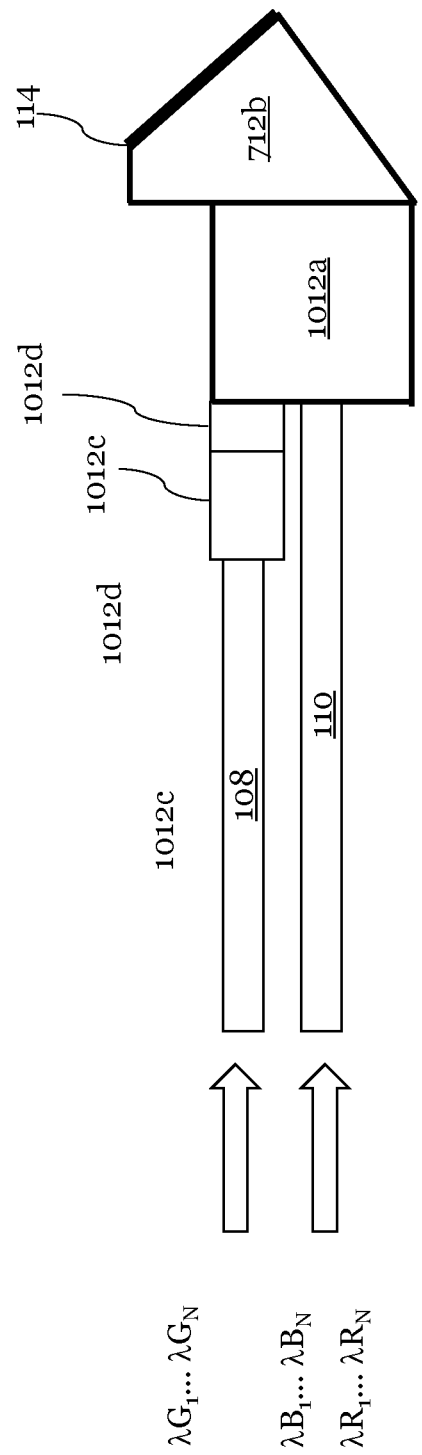
FIG. 11 is an illustration of a portion of an embodiment.

FIG. 11 is an illustration of a portion of an embodiment in which the High NA lens is used on one of the waveguides 108 or 110 that is substantially similar to the probe illustrated in FIG. 7 with a forward view design instead of the side view design illustrated in FIG. 10. High NA lens is inserted only between illumination waveguide 108 for green light and the collimation lens 1012a to increase NA of green light. Blue light and red light should have difference in their incident angles relative to the green light which is large enough for illumination overlap on sample. That can make it challenging to increase NA for all the illumination light between illumination waveguide 108 and spacer 712b. The blue light, red light, and green light should not hit grating 114 directly without reflection by mirror surface of the spacer 712b. Human eyes are more sensitive to green light than blue/red light. Therefore, it may be reasonable to make the NA larger for green light than for blue light or red light to obtain higher resolution for green in image than for blue and red. In one embodiment, the NA of the blue light and red light may be 0.11 as it is incident on the lens 1012a and the NA for the green light as it is incident on the lens 1012a may be 0.27.

Sixth Embodiment

Figure 12:
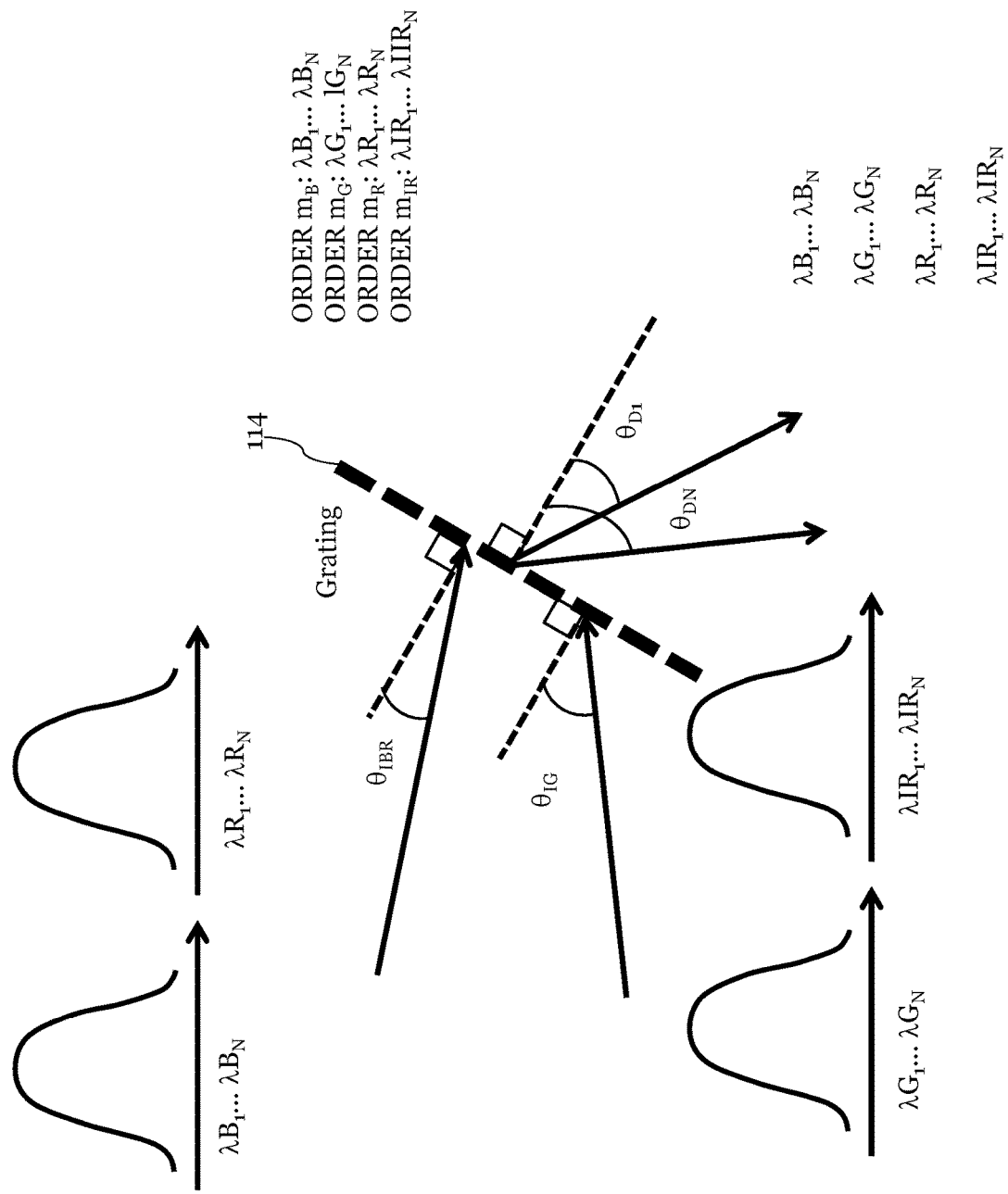
FIG. 12 is an illustration of light being diffracted in a portion of an embodiment.

FIG. 12 is an illustration of another embodiment, which is substantially similar to the other embodiment except that four channels are used. The four channels for example, might be Blue, Green, Red, and Infrared. The infrared information can be used to provide additional infrared information simultaneously with the RGB color imaging. Also it may be used for compensation of color matching in RGB imaging. For example, the wavelength for $\lambda G_1 \ldots \lambda G_N$ may be 500 nm-575 nm; $\lambda R_1 \ldots \lambda R_N$ may be 622.5 nm-735 nm; $\lambda B_1 \ldots \lambda B_N$ may be 415 nm-490 nm; and infrared color $\lambda IR_1 \ldots \lambda IR_N$ may be 750 nm-862.5 nm.

In an embodiment, the splitter 106 splits light from the light source 102, so that the blue light and the red light are coupled into the illumination waveguide 110 and the green light and the infrared light are coupled into the illumination waveguide 108. The order of diffraction for the blue light $m_B$ is different from the order of diffraction for the red light $m_R$. Also the order of diffraction for the green light $m_G$ is different from the order of diffraction for the infrared light $m_{IR}$. Order of diffraction used for blue, green, red, and infrared ($m_B$, $m_G$, $m_R$, $m_{IR}$) can be (3, 3, 2, 2) respectively.

Waveguide Offset

Figure 13:
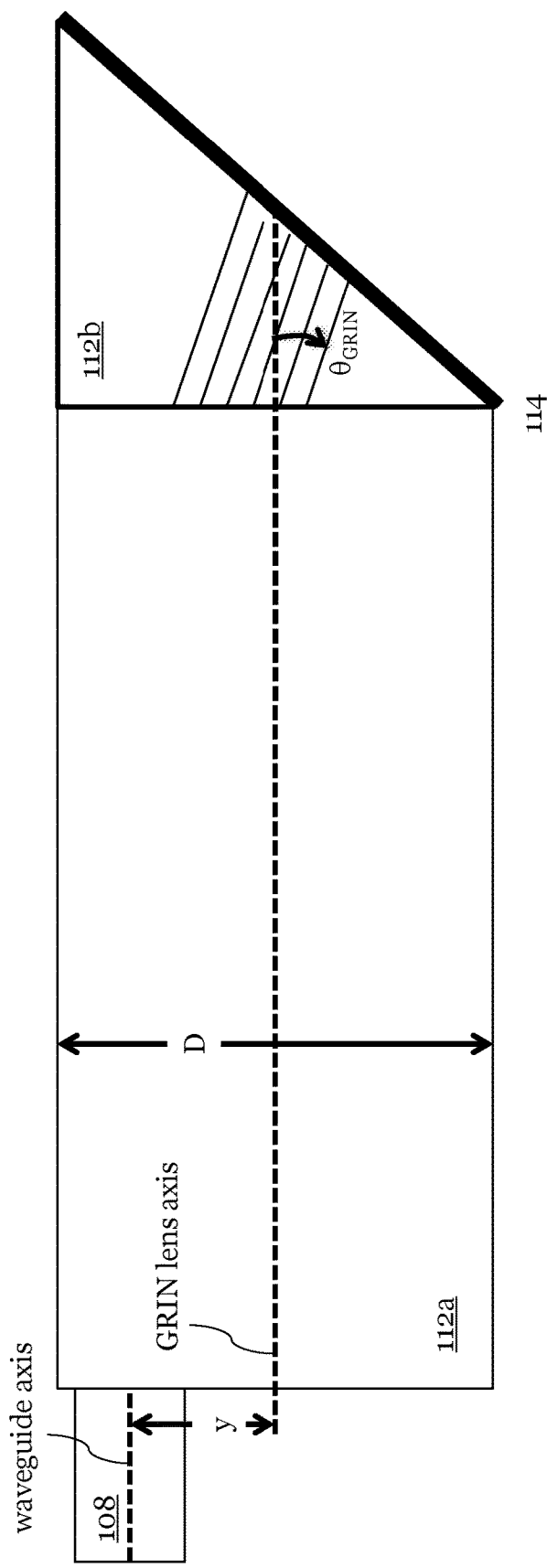
FIG. 13 is an illustration of a portion of an embodiment.

FIG. 13 is an illustration of a portion of an embodiment. In an embodiment, the incident angles $\theta_{I_G}$ and $\theta_{I_{BR}}$ may be controlled by adjusting offsets $y_G$ and $y_{BR}$ of the centers of the waveguides (108, 110) relative to the center of the GRIN lens 112a. The diameter (D) of the GRIN lens may be 500 µm. The pitch of GRIN lens may be around 0.25 in which case the light exiting the GRIN lens may be approximately collimated. An angle $\theta_{GRIN}$ between collimated light and GRIN lens axis may be calculated using equation (12) below.

$$\sin\theta_{GRIN} = 2y \frac{NA}{n_l D} \tag{12}$$

A value of $\theta_{GRIN}$ for each waveguide may be calculated based on $\theta_{I_G}$, $\theta_{I_{BR}}$, and the properties of the spacer 112b. This may then be used to calculate the offsets for each waveguide. When the edge of the waveguide is not on the front surface of the GRIN lens 112a, such as when coreless fiber is inserted between the waveguide and the GRIN lens 112a then the GRIN lens pitch may be a little smaller than 0.25 (e.g. 0.23). Ray tracing may be used to get a more accurate value for the offset.

Chromatic Dispersion

In the description above, the chromatic dispersion of optical material used to make the optical components of the optical system (e.g. GRIN lens 112a, spacer 112b) is ignored. If there is chromatic dispersion, that is the refractive index of material in optical path varies depending on wavelength. The combination of wavelengths of illumination light which is incident on the same location of sample will be slightly shifted from the combination described above. Such a wavelength shift may be compensated for during the image reconstruction process by the image processor 122.

For the compensation, a calibration step may be applied before imaging. For example, using a black-and-white target sample whose pattern is already known, three 2D images of red (124r), green (124g), and blue (124b) of the target can be obtained with the endoscope 110. The pattern may be a grid pattern or concentric circles. By comparing the target pattern and the obtained three 2D images, the relationships between the wavelengths and the view angles can be determined. This relationship will include any wavelength shift due to material dispersion, when this relationship is applied during image reconstruction, the wavelength shifts can be compensated for.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An apparatus comprising:
    illumination waveguides comprising only a first waveguide and a second waveguide;
    a coupler or connector disposed on or as part of the first waveguide, the coupler or connector operating to connect to a first light source and/or an optical splitter for obtaining or receiving at least a first wavelength band of light;
    a coupler or connector disposed on or as part of the second waveguide; and
    a diffractive element;
    wherein the first waveguide guides the first wavelength band of light onto the diffractive element such that the first wavelength band is diffracted at an $m^{th}$ non-zero order over a first range of angles;
    wherein the second waveguide guides a second wavelength band of light onto the diffractive element such that the second wavelength band of light is diffracted at the $m^{th}$ non-zero over the first range of angles;
    wherein the second waveguide guides a third wavelength band of light onto the diffractive element such that the third wavelength band of light is diffracted at an $n^{th}$ non-zero order over the first range of angles;
    wherein wavelengths of the first wavelength band, the second wavelength band, and the third wavelength band do not overlap with each other;
    wherein the $m^{th}$ order and the $n^{th}$ order are different from each other; and
    wherein the only illumination waveguides in the apparatus are the first waveguide and the second waveguide of the illumination waveguides.

2. The apparatus according to claim 1 wherein the first wavelength band is between the second wavelength band and the third wavelength band.

3. The apparatus according to claim 1 wherein:
    the first wavelength band of light is incident on the diffractive element at a first angle;
    the second wavelength band of light is incident on the diffractive element at a second angle; and
    the third wavelength band of light is incident on the diffractive element at the second angle.

4. The apparatus according to claim 3, wherein the apparatus operates to adjust offsets of respective centers of the first waveguide and the second waveguide to control the first incident angle and the second incident angle.

5. The apparatus according to claim 1 wherein:
    the first wavelength band of light includes green light;
    the second wavelength band includes blue light; and
    the third wavelength band includes red light.

6. The apparatus according to claim 1 wherein:
    the first wavelength band of light includes green light;
    the second wavelength band includes red light; and
    the third wavelength band includes blue light.

7. The apparatus according to claim 1 wherein n is equal to m minus one.

8. The apparatus according to claim 1 wherein n is equal to m plus one.

9. The apparatus according to claim 1 further comprising:
    an optical splitter,
    wherein the optical splitter splits light from a light source into the first wavelength band of light which is guided by the first waveguide, and the second wavelength band and third wavelength band of light both of which are guided by the second waveguide, and
    the optical splitter includes a first output port and a second output port, the first output port operating to send the first wavelength band of light to the first waveguide, and the second output port operating to send the second wavelength band of light and the third wavelength band of light to the second waveguide.

10. The apparatus according to claim 9 further comprising the light source.

11. The apparatus according to claim 1 further comprising a detection waveguide for gathering light from a subject, wherein the subject has been illuminated with the first wavelength band, the second wavelength band of light, and the third wavelength band diffracted by the diffractive element over the first range of angles.

12. The apparatus according to claim 11, wherein the detection waveguide is a multimode fiber.

13. The apparatus according to claim 11, wherein the detection waveguide guides the gathered light to a spectrometer.

14. The apparatus according to claim 13, further comprising the spectrometer.

15. The apparatus according to claim 14, wherein the spectrometer includes one or more detectors for converting the gathered light into an electrical signal which is then converted into a digital signal which then used to create an image of the subject.

16. The apparatus according to claim 11, wherein the diffracted light is scanned across the subject perpendicular to a line formed by the first range of angles.

17. The apparatus according to claim 16, wherein the diffracted light is scanned in a linear manner to form a planar image or in rotational manner to form a toroidal image.

18. The apparatus according to claim 17, further comprising a moveable optical element located after the diffraction grating that scans the diffracted light.

19. The apparatus according to claim 17, wherein a portion of the apparatus including at least the diffraction grating is moved to scan the diffracted light.

20. The apparatus according to claim 1, wherein
the first wavelength band includes light with a wavelength of 540 nm;
the second wavelength band includes light with a wavelength of 450 nm;
the third wavelength band includes light with a wavelength of 675 nm;
the $m^{th}$ order is 3 or −3;
the $n^{th}$ order is 2 or −2; and
and sgn($m^{th}$ order) is equal to sgn($n^{th}$ order).

21. The apparatus according to claim 1, wherein
the first wavelength band includes light with a wavelength of 540 nm;
the second wavelength band includes light with a wavelength of 675 nm;
the third wavelength band includes light with a wavelength of 450 nm;
the $m^{th}$ order is 2 or −2;
the $n^{th}$ order is 3 or −3; and
sgn($m^{th}$ order) is equal to sgn($n^{th}$ order).

22. The apparatus according to claim 1, further comprising:
a beam blocker, wherein the beam blocker prevents light that leaves the diffractive element at angles that are not within the first range of angles from illuminating a sample and allows light that leaves the diffractive element at angles that are within the first range of angles to illuminate the sample.

23. The apparatus according to claim 1, wherein the numerical aperture of light of the first waveguide as it is incident on the diffractive element is different from the numerical aperture of light of the second waveguide as it is incident on the diffractive element.

24. The apparatus according to claim 1, further comprising a rotary splitter, wherein the rotary splitter:
receives light from the light source;
guides the first wavelength band of light from a light source to the first waveguide;
guides the second wavelength band of light and the third wavelength band of light from the light source to the second waveguide; and
allows the first waveguide, the second waveguide and other optical components to rotate relative to the light source while allowing light to be guided from the light source to both of the first waveguide and the second waveguide.

25. The apparatus according to claim 1, wherein
the first waveguide guides a fourth wavelength band of light onto the diffractive element such that the fourth wavelength band of light is diffracted at the $n^{th}$ non-zero order over the first range of angles; and
wherein wavelengths of the first wavelength band, the second wavelength band, the third wavelength band, and the fourth wavelength band do not overlap with each other.

26. The apparatus according to claim 25, wherein:
the first wavelength band includes light with a wavelength of 540 nm;
the second wavelength band includes light with a wavelength of 450 nm;
the third wavelength band includes light with a wavelength of 675 nm;
the fourth wavelength band includes light with a wavelength of 810 nm;
the $m^{th}$ order is 3 or −3;
the $n^{th}$ order is 2 or −2; and
sgn($m^{th}$ order) is equal to sgn($n^{th}$ order).

27. The apparatus according to claim 1, wherein the coupler or connector of the second waveguide operates to connect to one or more of the following:
(i) at least one second light source for producing or providing the second wavelength band of light and the third wavelength band of light, wherein the at least one second light source comprises one or more of the following: (a) a second light source that operates to produce or provide the second wavelength band of light and the third wavelength band of light, (b) a second light source that operates to produce or provide the second wavelength band of light and a third light source that operates to produce or provide the third wavelength band of light, and/or (c) a light source having a notch filter; and/or
(ii) the optical splitter for obtaining or receiving the second and third wavelength bands of light through the optical splitter.

28. The apparatus according to claim 1, wherein one or more of the following:
(i) the first wavelength band, the second wavelength band, and the third wavelength band overlap each other on a sample or overlap each other at a same spatial location on a sample; and/or
(ii) the first wavelength band, the second wavelength band, and the third wavelength band completely overlap each other on a sample or completely overlap each other at a same spatial location on a sample.

* * * * *